(12) United States Patent
Kalyanaraman et al.

(10) Patent No.: US 8,962,600 B2
(45) Date of Patent: Feb. 24, 2015

(54) NEUROPROTECTIVE COMPOUNDS AND THEIR USE

(75) Inventors: Balaraman Kalyanaraman, Wauwatosa, WI (US); Joy Joseph, New Berlin, WI (US); Anumantha Kanthasamy, Ames, IA (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 297 days.

(21) Appl. No.: 13/266,659

(22) PCT Filed: Apr. 15, 2010

(86) PCT No.: PCT/US2010/031296
§ 371 (c)(1),
(2), (4) Date: Jan. 13, 2012

(87) PCT Pub. No.: WO2010/126719
PCT Pub. Date: Nov. 4, 2010

(65) Prior Publication Data
US 2012/0108549 A1 May 3, 2012

Related U.S. Application Data

(60) Provisional application No. 61/172,842, filed on Apr. 27, 2009.

(51) Int. Cl.
*A61K 31/66* (2006.01)
*C07F 9/54* (2006.01)
*A61P 25/16* (2006.01)
*A61P 39/06* (2006.01)
*C07C 69/34* (2006.01)
*C07C 69/017* (2006.01)

(52) U.S. Cl.
CPC .............. *C07C 69/34* (2013.01); *C07C 69/017* (2013.01); *C07F 9/5407* (2013.01); *C07F 9/5442* (2013.01)
USPC ........... 514/107; 514/130; 514/120; 514/121; 514/124; 514/119; 514/134; 568/11; 568/10; 568/17; 568/15

(58) Field of Classification Search
CPC ...... A61K 31/66; C07F 9/5442; C07F 9/5449
USPC ......... 514/107, 130, 120, 121, 124, 119, 134; 568/11, 10, 17, 15
See application file for complete search history.

(56) References Cited

U.S. PATENT DOCUMENTS 6,331,532 B1 * 12/2001 Murphy et al. ............... 514/100
2007/0066572 A1 * 3/2007 Balaraman et al. ............. 514/89

FOREIGN PATENT DOCUMENTS

CN 1861060 11/2006

OTHER PUBLICATIONS

Delogu et al. Tetrahedron 2004, 60 (45), 10305-10310.*
Murphy, M. Trends Biotechnology 1997, 15, 326-330.*
Rautio et al. Nature Reviews 2008, 7, 255-270.*
Haynes et al. J. Chem. Soc. 1956, 2823-2831.*
International Search Report and Written Opinion mailed Aug. 11, 2010 (International Patent Application No. PCT/US2010/031296; filed on Apr. 15, 2010).
Boillee et al., "Revisiting oxidative damage in ALS: microglia, Nox, and mutant SOD1" The Journal of Clinical Investigation, vol. 118, No. 2 (2008) pp. 474-478.
Harraz et al., "SOD1 mutations disrupt redox-sensitive Rac regulation of NADPH oxidase in a familial ALS model", Journal of Clinical Investigation, vol. 118, No. (2008) pp. 659-670.
Stefanska et al., "Apocynin:molecular aptitudes", Mediators of Inflammation, vol. 2008 (2008) pp. 106507-1-106507-10).
Moiseev et al., "Reactions of tertiary phosphines with alcohols in aqueous media", Inorganic Chemistry, vol. 48, No. 1 (Jan. 5, 2009) pp. 239-245.
Moiseev et al., "Interaction of tertiary phosphines with lignin-type, alpha, beta-unsaturated aldehydes in water" Inorganic Chemistry, vol. 46, No. 2 (Oct. 29, 2007) pp. 9389-9399.
Li et al., "Nasal formulation for treating Alzheimer's disease, improving memory, and adjusting permeability of blood-brain barrier", Database CA [Online] Chemical Abstracts Service, (2006) Database accession No. 146:50245.
Matsushita et al., "gamma-selective Hydroxlation of alpha-beta, gamma, delta-Unsaturated Carbonyl Compounds and its Application to Syntheses of (+—)—6—Hydroxshogaol and Related Furnaoids", Tetrahedron Letter, vol. 36, No. 11 (1995) pp. 1879-1882).

* cited by examiner

*Primary Examiner* — Sreeni Padmanabhan
*Assistant Examiner* — Irina Neagu
(74) *Attorney, Agent, or Firm* — Quarles & Brady LLP

(57) ABSTRACT

Apocynin derivative compounds, active pharmaceutical ingredients, dosage forms, and methods of use thereof as neuroprotectants in the brain of mammals.

9 Claims, 20 Drawing Sheets

NEUROPROTECTIVE COMPOUNDS AND THEIR USE

CROSS REFERENCE TO RELATED APPLICATIONS

This Application represents the national stage application of International Application No. PCT/US2010/031296 filed Apr. 15, 2010, which claims priority to U.S. Provisional Application No. 61/172,842, filed Apr. 27, 2009, both of which are incorporated by reference herein in their entirety for all purposes.

STATEMENT OF GOVERNMENT INTEREST

This invention was funded by the U.S. National Institute of Health under the following grants or contract numbers: R01 NS039958 and R01 NS04094. The United States government has certain rights in this invention.

BACKGROUND OF THE INVENTION

Experimental models of mitochondrial diseases typically involve inhibition of enzymes involved in the electron transport chain (1). It has been further reported that many neurodegenerative diseases are associated with mitochondrial dysfunction (2-5). Defects in complexes I, II and IV of the mitochondrial respiratory chain have been detected in Alzheimer's, Parkinson's, Huntington's and Lou Gehrig's diseases (6-9).

Several lines of evidence implicate that Parkinson's Disease (PD) is a free radical disease involving mitochondrial dysfunction leading to failure of energy production (10-11). Increased oxidative damage, dopamine depletion, protein nitration, iron accumulation, protein aggregation, and apoptosis are characteristic hallmarks of Parkinson's Disease (12-14).

Numerous antioxidants and iron chelators have been utilized in Parkinson's Disease animal models and patients with little or limited success (15-16). Apocynin is a naturally occurring methoxy-substituted catechol that has been shown to inhibit NADPH-oxidase (17). Apocynin has the structure depicted below:

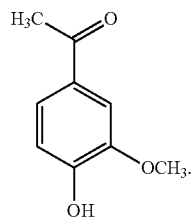

Apocynin has also been reported to form a dimer by peroxidase oxidation (17), such as depicted below:

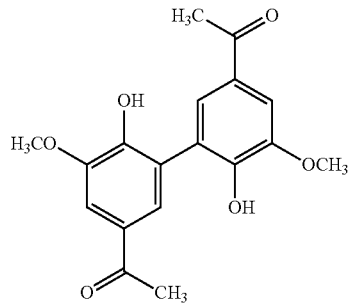 [SMILES: COc1cc(C(C)=O)cc(-c2cc(C(C)=O)cc(OC)c2O)c1O]

While the usefulness of various apocynin derivatives has been reported in the literature (2-5), their potential as therapeutic drugs in neurodegenerative diseases, such as Parkinson's disease, has not been established.

SUMMARY OF THE INVENTION

One aspect of the invention is an apocynin derivative according to the structure:

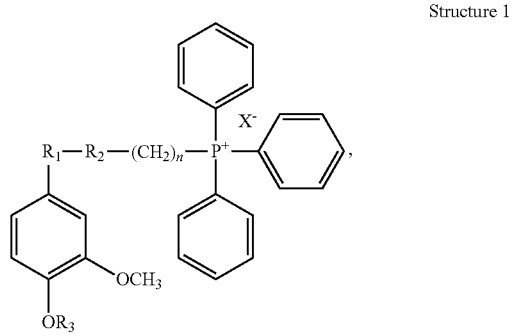

Structure 1 wherein $R_1$ is C=O, (CH=CH) or $CH_2$, wherein $R_2$ is O, NH or COO, wherein $R_3$ is H, $COCH_3$ or $CO(CH_2)_m CH_3$, wherein $X^-$ is $Cl^-$, $Br^-$, or $I^-$, wherein n is 2-16, and wherein m is 1-16, or a prodrug, solvate or hydrate thereof. As used herein, apocynin derivative compounds may be active pharmaceutical ingredients.

Another aspect of the invention is a pharmaceutical dosage form comprising the apocynin derivative of Structure 1 and a pharmaceutically suitable carrier system.

Another aspect of the invention is the pharmaceutical dosage form of Structure 1, wherein the dosage form comprises an oral, injection, infusion, inhalation, transdermal, or implant dosage form.

Another aspect of the invention is a method of increasing the amount of dopamine in the brain of a mammal comprising administering a therapeutically effective amount of the apocynin derivative Structure 1.

Another aspect of the invention is a method of increasing the amount of dopac in the mitochondria of a mammalian brain cell comprising administering a therapeutically effective amount of the apocynin derivative Structure 1.

Another aspect of the invention is an apocynin derivative according to any one of the following structures:

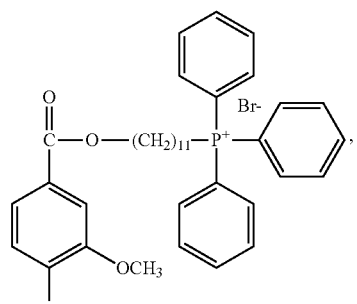

(vanillic acid derivative, Structure 2)

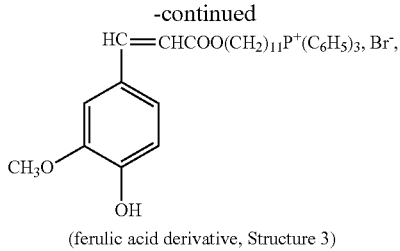

(ferulic acid derivative, Structure 3)

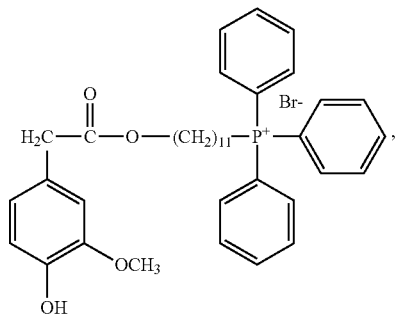

(homovanillic acid derivative, Structure 4)

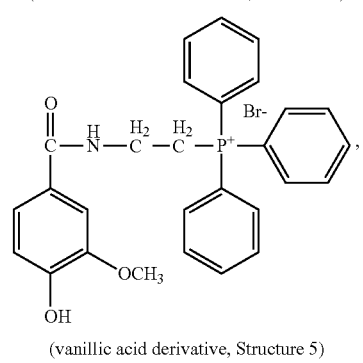

(vanillic acid derivative, Structure 5)

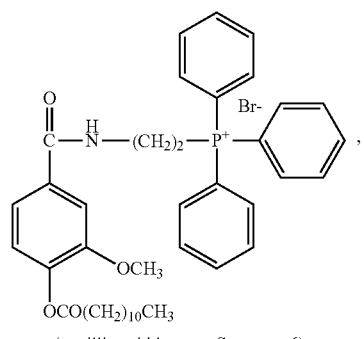

(vanillic acid laurate, Structure 6)

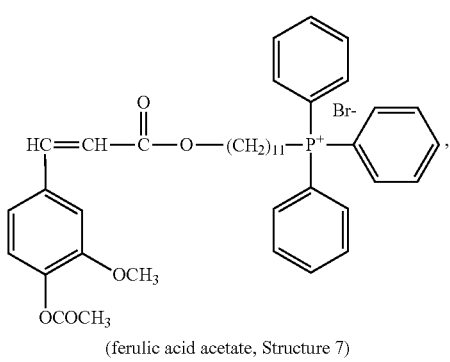

(ferulic acid acetate, Structure 7)

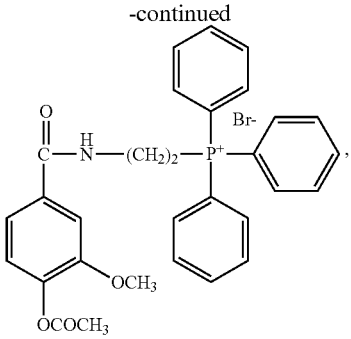

(vanillic acid acetate, Structure 8)

or a prodrug, solvate or hydrate thereof.

Another aspect of the invention is a pharmaceutical dosage form comprising at least one of Structures 2-8 and a pharmaceutically suitable carrier system.

Another aspect of the invention is the pharmaceutical dosage form of at least one of Structures 2-8 wherein the dosage form comprises an oral, injection, infusion, inhalation, transdermal, or implant dosage form.

Another aspect of the invention is a method of increasing the amount of dopamine in the brain of a mammal comprising administering a therapeutically effective amount of at least one of Structures 2-8.

Another aspect of the invention is a method of increasing the amount of dopac in the mitochondria of a mammalian brain cell comprising administering a therapeutically effective amount of at least one of Structures 2-8.

In one aspect of the methods-identified above, which relate to increasing the amount of dopamine in the brain of a mammal or the amount of dopac in the mitochondria of a mammalian brain cell, Structures 1-8 are orally administered.

Another aspect of the invention is an apocynin derivative according to the structure:

Structure 9

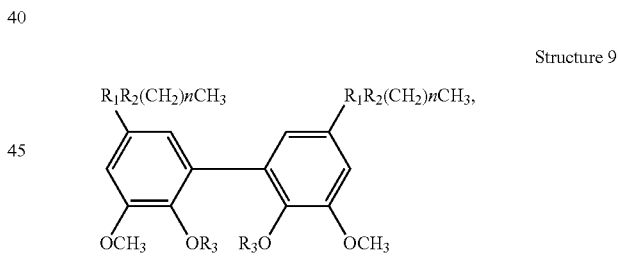

wherein $R_1$ is C=O, $CH_2$, or (CH=CH), wherein $R_2$ is O, NH or COO, wherein $R_3$ is H, $COCH_3$ or $CO(CH_2)_m CH_3$, wherein n is 2-16, and wherein m is 1-16, or a prodrug, salt, solvate or hydrate thereof.

Another aspect of the invention is a pharmaceutical dosage form including Structure 9 and a pharmaceutically suitable carrier system.

A further aspect of the invention is the pharmaceutical dosage form of Structure 9, wherein the dosage form comprises an oral, injection, infusion, inhalation, transdermal, or implant dosage form.

Another aspect of the invention is a method of increasing the amount of dopamine in the brain of a mammal comprising administering a therapeutically effective amount of Structure 9.

A further aspect of any of the methods herein is that Structure 9 is orally administered.

Another aspect of the invention is a method of increasing the amount of dopac in the mitochondria of a mammalian brain cell comprising administering a therapeutically effective amount of Structure 9.

Another aspect of the invention is the apocynin derivative according to the structure:

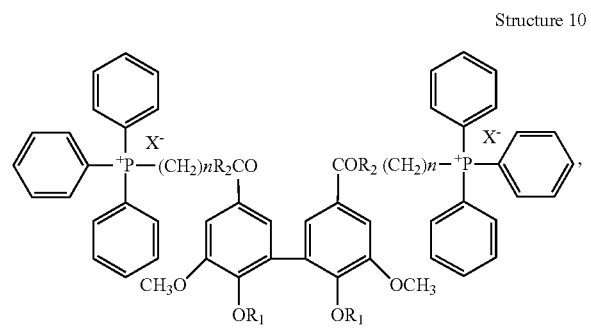

Structure 10 wherein $R_1$ is H, $COCH_3$, or $CO(CH_2)_mCH_3$, wherein $R_2$ is O or NH, wherein $X^-$ is $Cl^-$, $Br^-$ or $I^-$, wherein n is 2-16, and wherein m is 1-16, or a prodrug, solvate or hydrate thereof.

Another aspect of the invention is an apocynin derivative of Structure 10 wherein $R_1$ is H, $COCH_3$, or $CO(CH_2)_mCH_3$, wherein $R_2$ is O or NH, wherein $X^-$ is $Br^-$, wherein n is 2-16, and wherein m is 1-16, or a prodrug, salt, solvate or hydrate thereof.

In a further aspect of the invention, a pharmaceutical dosage form comprises at least one of Structure 10, a derivative thereof and a pharmaceutically suitable carrier system.

Another aspect of the present invention is the pharmaceutical dosage form of Structure 10 or a derivative thereof, wherein the dosage form comprises an oral, injection, infusion, inhalation, transdermal, or implant dosage form.

A further aspect of the present invention is a method of increasing the amount of dopamine in the brain of a mammal comprising administering a therapeutically effective amount of Structure 10 or a derivative thereof.

A further aspect of any of the methods herein is that Structure 10 or a derivative thereof is orally administered.

Another aspect of the invention is a method of increasing the amount of dopac in the mitochondria of a mammalian brain cell comprising administering a therapeutically effective amount of Structure 10 or derivative thereof.

Another aspect of the invention is an apocynin derivative according to the structure:

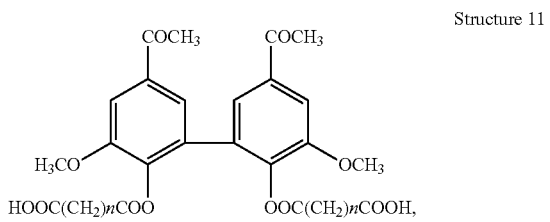

Structure 11 wherein n is 1-16, or a prodrug, solvate or hydrate thereof.

A further aspect of the invention is a pharmaceutical dosage form comprising Structure 11 and a pharmaceutically suitable carrier system.

Another aspect of the invention is the pharmaceutical dosage form of Structure 11, wherein the dosage form comprises an oral, injection, infusion, inhalation, transdermal, or implant dosage form.

Another aspect of the invention is a method of increasing the amount of dopamine in the brain of a mammal comprising administering a therapeutically effective amount of Structure 11.

Another aspect of the invention is a method of increasing the amount of dopac in the mitochondria of a mammalian brain cell comprising administering a therapeutically effective amount of Structure 11.

A further aspect of any of the methods herein is that Structure 11 is orally administered.

Another aspect of the invention is an apocynin derivative according to the structure:

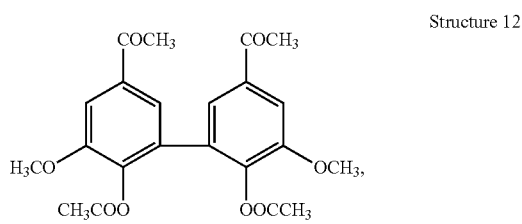

Structure 12 or a prodrug, salt, solvate or hydrate thereof.

A further aspect of the invention is a pharmaceutical dosage form comprising Structure 12 and a pharmaceutically suitable carrier system.

Another aspect of the invention is the pharmaceutical dosage form of Structure 12, wherein the dosage form comprises an oral, injection, infusion, inhalation, transdermal, or implant dosage form.

A further aspect of the invention is a method of increasing the amount of dopamine in the brain of a mammal comprising administering a therapeutically effective amount of Structure 12.

Another aspect of the invention is a method of increasing the amount of dopac in the mitochondria of a mammalian brain cell comprising administering a therapeutically effective amount of Structure 12.

A further aspect of any of the methods herein is that Structure 12 is orally administered.

Another aspect of the invention is a method of reducing brain inflammation or the effects thereof in a mammal, comprising administering to the mammal an effective amount of an apocynin derivative to reduce brain inflammation or the effects thereof relative to an untreated animal with brain inflammation. In this method the apocynin derivative comprises at least one of apocynin, diapocynin, diapocynin-acetate, diapocynin-diacetate, mito-apocynin, mito-diapocynin, apocynin-acetate, mito-apocynin-acetate, mito-diapocynin-acetate, and mito-diapocynin-diacetate.

Another aspect of the invention is a method of preventing pathophysiological neurotransmitter deficit associated with brain inflammation in a patient, comprising administering an effective amount of an apocynin derivative to the patient to prevent pathophysiological neurotransmitter deficit. In this method the apocynin derivative comprises at least one of apocynin, diapocynin, diapocynin-acetate, diapocynin-diacetate, mito-apocynin, mito-diapocynin, apocynin-acetate, mito-apocynin-acetate, mito-diapocynin-acetate, and mito-diapocynin-diacetate.

Another aspect of the invention is method of preventing a decrease in dopamine levels in the brain of a patient with Parkinson's disease, comprising administering an effective amount of an apocynin derivative to the patient to prevent the decrease in dopamine levels. In this method the apocynin derivative comprises at least one of apocynin, diapocynin, diapocynin-acetate, diapocynin-diacetate, mito-apocynin, mito-diapocynin, apocynin-acetate, mito-apocynin-acetate, mito-diapocynin-acetate, and mito-diapocynin-diacetate.

Another aspect of the present invention is a method of delaying neurodegeneration in a mammal, comprising administering an effective amount of an apocynin derivative to the mammal, wherein the neurodegeneration is caused by at least one of neural inflammation, Huntington's disease, Parkinson's disease, amyotrophic lateral sclerosis, multiple sclerosis, and Alzheimer's disease, and wherein the delay in neurodegeneration postpones the onset or lessens the effect of disease symptoms associated with at least one of neural inflammation, Huntington's disease, Parkinson's disease, amyotrophic lateral sclerosis, multiple sclerosis, and Alzheimer's disease. In this method the apocynin derivative comprises at least one of apocynin, diapocynin, diapocynin-acetate, diapocynin-diacetate, mito-apocynin, mito-diapocynin, apocynin-acetate, mito-apocynin-acetate, mito-diapocynin-acetate, and mito-diapocynin-diacetate.

Another aspect of the present invention is a method of prolonging motor function in a mammal with a neurodegenerative disease, comprising administering an effective amount of an apocynin derivative to the mammal to prolong motor function in the mammal. In this method the apocynin derivative comprises at least one of apocynin, diapocynin, diapocynin-acetate, diapocynin-diacetate, mito-apocynin, mito-diapocynin, apocynin-acetate, mito-apocynin-acetate, mito-diapocynin-acetate, and mito-diapocynin-diacetate.

As used herein, an oral dosage form includes a pharmaceutically suitable oral carrier system, an injection dosage form includes a pharmaceutically suitable injection carrier system, an infusion dosage form includes a pharmaceutically suitable infusion carrier system, an inhalation dosage form includes a pharmaceutically acceptable inhalation carrier system (and/or a pharmaceutically suitable inhalation device), an the transdermal dosage form includes a pharmaceutically suitable transdermal carrier system (and/or a pharmaceutically suitable transdermal device). Further, an implant dosage form includes medical devices for temporary or permanent attachment to or implant within a patient, including, for example, a stent, catheter, shunt, electrode, electrical device, reservoir, or medical implement, that is coated, impregnated, or filled with or that dispenses an apocynin derivative.

DETAILED DESCRIPTION

The reasons for the death of dopaminergic (dopamine producing) neuronal cells are not known. Proposed mechanisms include genetic mutation, chronic inflammation, and exposure to environmental toxicants. It is hypothesized that activation of resident immune cells in the brain (called microglia) by inflammatory mediators (molecules overproduced during inflammation) contributes to the death or degeneration of neurons (18-19). Support for this hypothesis came from postmortem studies on brains taken from PD patients that showed enhanced levels of cytotoxic, proinflammatory mediators (18). Patients who developed PD following the accidental exposure to MPTP, a contaminant by-product of an illicit narcotic, also exhibited activated microglial cells in the substantia nigra (20). Proinflammatory mediators (TNF-α, IL-1, IL-6, were also detected in the cerebrospinal fluid of PD patients (18). Proinflammatory mediators that activate microglia include cytokines such as the tumor necrosis factor-alpha (TNF-α), interleukin-1beta (IL-1β), interleukin-6 (IL-6), and interferon gamma, chemokines (MCP-1), reactive oxygen species (ROS) and reactive nitrogen species (RNS), including nitric oxide and oxidants derived from nitric oxide and superoxide, oxidative enzymes such as NADPH oxidase, cyclooxygenase-2 (COX-2), myeloperoxidase, and prostaglandins. Oxidative enzymes (for example, COX-2 and inducible NOS) are likely stimulated by proinflammatory cytokines. Similar proinflammatory changes and neuroinflammatory processes were also reproduced in animal models of PD (18).

Neuroprotective drugs can be broadly classified as agents that can mitigate the effects of brain inflammation including mitochondrial oxidative and nitrosative damage in the brain, enhance and/or prevent decreases in or deficits in neurotransmitter levels, such as, for example, neuronal dopamine levels, or prevent microglial and astroglial activation and inhibit cytokine release in the brain-processes associated with neuroinflammation. As a result, neuroprotective drugs may inhibit or delay neurodegeneration which, in turn, may postpone the onset or lessen the effects of neurodegenerative disease symptoms. For example, administration of neuroprotectants may prolong motor function in animals with neurodegenerative diseases permitting them to maintain normal or near normal function for longer periods of time compared to convention therapies. Anti-inflammatory strategies to reverse neuroinflammation in other neurodegenerative diseases (e.g. PD, Alzheimer's disease) are currently being investigated (21-23). In light of the apparent connection between many neurodegenerative diseases and mitochondrial dysfunction (2-14), neuroprotective compounds that target mitochondria may prove particularly useful.

Figure 2:
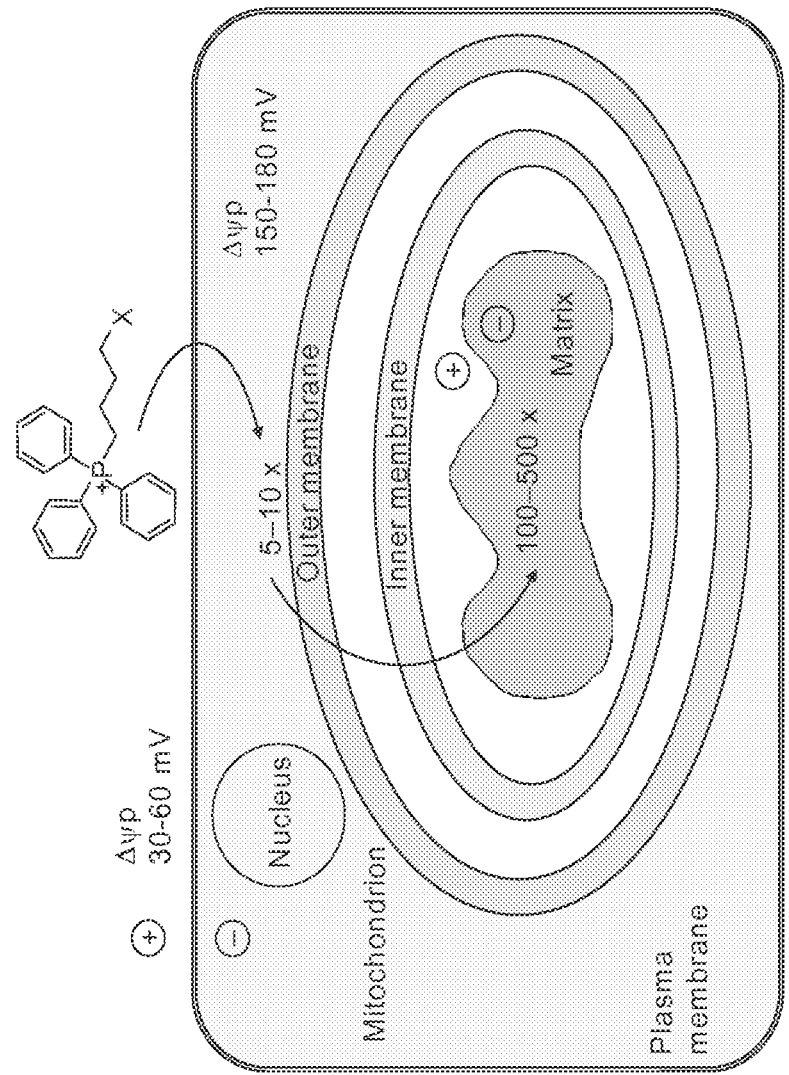
FIG. 2 is a schematic of a eukaryotic cell illustrating the mitochondrial accumulation of targeted cationic antioxidants facilitated by the large negative membrane potential.

Conventional ROS detoxification probes (such as Vitamin-E, tempol, ubiquinone) do not significantly accumulate within mitochondria, so their ability to scavenge mitochondrial ROS (superoxide, peroxyl radical) is limited. It has been reported that antioxidants (such as Vitamin-E and Coenzyme-Q) coupled to a triphenylphosphonium cation are accumulated into mitochondria (24-26). The uptake of such lipophilic, membrane-permeable cations into cells from the extracellular space is favored by the plasma membrane potential (30-60 mV, negative inside). As shown in FIG. 2, the large membrane potential of 150-180 mV (negative inside) across the mitochondrial inner membrane enables the redistribution of lipophilic cations from the intracellular space into the mitochondria. (27). From the equation, membrane potential (mV)=61.5 $\log_{10}(C/C_o)$, it can be estimated that for every 61.5 mV difference in the membrane potential, there is a 10-fold increase in the mitochondrial concentration of the lipophilic cations leading to a 100- to 500-fold higher concentration of the cation in the mitochondria than in the cytosol (27).

An important aspect of the invention is use of the lipophilic cation approach to discover mitochondria-targeted nitroxides in neurons subjected to oxidative stress that are capable of restoring dopamine levels in those neurons undergoing oxidative stress. Alkylphosphonium nitroxides have been used to measure transmembrane potentials and membrane dynamics (28). It was recently reported that alkylphosphonium nitroxide (for example, Mito-CP) could be targeted to mitochondria (29). The selective uptake of Mito-CP into the mitochondria was responsible for inhibiting peroxide-induced iron signaling, oxidative damage, and apoptosis in endothelial cells.

The blood brain barrier, which separates circulating blood from the cerebral spinal fluid, presents a challenge to pharmaceuticals with potentially beneficial effects for the central nervous system. Direct treatment of the cerebral spinal fluid is fraught with difficulties and potential complications, while introduction of pharmaceuticals into the circulatory system is routine. Therefore, it is more desirable to use compounds that sufficiently pass through the blood brain barrier for treatment of the central nervous system. To this end, certain pharmaceuticals may pass through the blood brain barrier if appropriately designed or encapsulated within liposomes. For example, long chain hydrocarbon moieties added to therapeutic molecules enable transport across the blood brain barrier. Suitable examples include diacetates, succinate, maleate, or glutarate derivatives, and longer chain hydrocarbon substituents. Without wishing to be bound by theory, it is likely that apocynin derivatives are taken up through specific receptors in the brain (for example, dopaminergic receptor, amino acid and glucose transporters).

High concentrations of apocynin, a plant-derived antioxidant, have been shown to protect against neuronal damage in SOD1 mutant ALS mice model (5). The instant invention contemplates that mitochondria-targeted apocynin might be effective in mitigating mitochondrial damage. Moreover, the instant invention contemplates the use of apocynin derivatives to combat inflammation, including neural inflammation, as well as Huntington's disease, Parkinson's disease, amyotrophic lateral sclerosis, multiple sclerosis, Alzheimer's disease, stroke, and diseases and/or injuries that promote or lead to oxidation-related sequelae.

Apocynin derivatives include apocynin and functional derivations thereof. For example, apocynin derivatives include diapocynin, mito-apocynin, mito-diapocynin, apocynin-acetate, apocynin-diacetate, mito-apocynin-acetate, mito-apocynin-diacetate, mito-diapocynin-acetate, and mito-diapocynin-diacetate, and as defined otherwise herein. Additional apocynin derivatives include acetates, diacetates, diglutarates, and diadepates, for example, diapocynin diacetates, diglutarates, and diadepates. In another embodiment, nanoparticulates of diapocynin and derivatives are contemplated.

Animal Model of Parkinson's Disease.

Epidemiological studies strongly suggest a link between pesticides that are mitochondrial toxins and the etiology of Parkinson's Disease (10). One of the frequently used animal models of Parkinson's Disease is the 1-methyl-4-phenyl-1,2,3,6-tetrahydropyridine (MPTP) model (30-31). MPTP was initially discovered as a contaminant of an illicit narcotic, and it has been reported to induce Parkinson-like symptoms in experimental animals (32-34).

Although the MPTP model of PD differs from idiopathic PD, there are many biochemical and pathological similarities (34-40). Selective destruction of dopaminergic neurons in the substantia nigra of the brain has also been reported (38).

Figure 1:
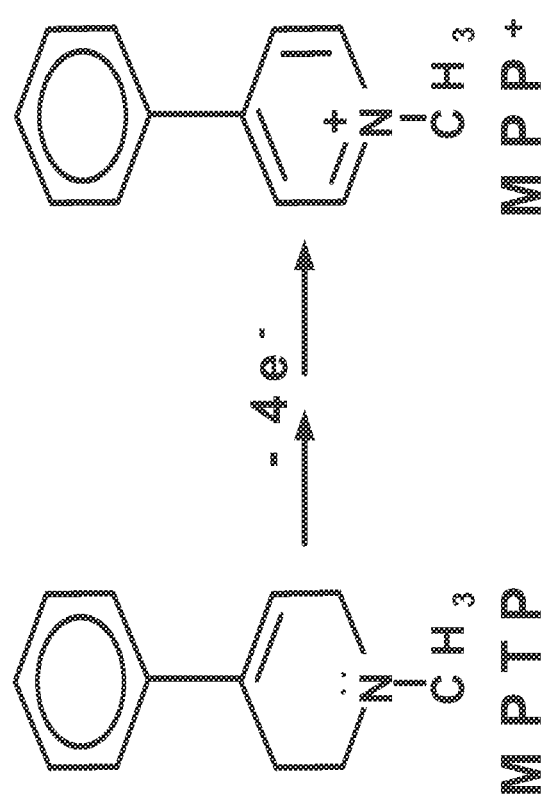
FIG. 1 illustrates the mono-amine oxidase-catalyzed oxidation of MPTP to MPP$^+$ via the intermediate, MPDP$^+$ (not shown)

The ultimate toxic metabolite of MPTP was determined to be 1-methyl-4-phenylpyridinium (MPP+) (see FIG. 1), which is accumulated selectively by neurons expressing the dopamine transporter (DAT) including the dopaminergic neurons of the substantia nigra. MPP+ impairs mitochondrial function by inhibiting complex I activity of the electron transport chain (41-43). Systemic inhibition of complex I was shown to cause Parkinsonism, reproducing the features of PD (44-46). Moreover, MPTP causes decreased mitochondrial complex I activity, increased reactive oxygen species (ROS), depletion of antioxidants, and activation of apoptotic signaling including mitogen-activated protein (MAP) kinases (31, 42, 47, and 48).

The MPTP C57 black mouse model is accepted as the best preclinical model of PD (49). Although the MPTP monkey model is often used for testing the efficacies of new therapies for PD, the MPTP mouse model is a reliable, cost effective model for probing the effectiveness of new therapies.

Although various MPTP treatment protocols have been reported, essentially two dosing regimens are well characterized. The acute model of MPTP (15 mg/kg MPTP administered intraperitoneally four times at 2 hr intervals) induces a stable and highly reproducible dopamine deficit but also severe overt toxicity. The subchronic or subacute model induces substantial apoptotic cell death without significant necrotic cell death using MPTP dose ranges that may vary from 18-30 mg/kg. In the subchronic model, mice received MPTP (20 mg/kg body weight, once a day for 5 days). Finally, the chronic MPTP mouse model mimics PD where the nigrostriatal dopaminergic neurons undergo destruction in a slow and progressive manner as occurs in idiopathic PD. In the chronic model, mice were administered with MPTP (25 mg/kg, twice/week, intraperitoneally) and probenecid (250 mg/kg) to prevent excretion for 5 weeks.

In general, the instant invention is directed to new chemical entities (NCEs) being active pharmaceutical ingredients (APIs), pharmaceutical compositions, dosage forms and method of making thereof. The invention also includes methods of using the APIs, pharmaceutical compositions and dosage forms thereof for use as neuroprotectants by increasing the amounts of dopamine and dopac in the brain and mitochondria of a mammal. The instant NCEs and APIs include apocynin derivatives, including for example, mito-apocynin derivative compounds and dimer mito-apocynin derivative compounds.

As used herein, "salts" of the instant compound may be a pharmaceutically suitable (i.e., pharmaceutically acceptable) salt including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those previously disclosed (50-51). For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, and triethiodide.

As used herein, "hydrates" of the instant compound may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc.

As used herein, "solvates" of the instant compound may be a pharmaceutically suitable (i.e., pharmaceutically acceptable) solvate, whereby solvation is an interaction of a solute with the solvent which leads to stabilization of the solute species in the solution, and whereby the solvated state is an ion in a solution complexed by solvent molecules. Solvates and hydrates may also be referred to as "analogues."

As used herein, "prodrugs" are compounds that are pharmacologically inert but are converted by enzyme or chemical action to an active form of the drug (i.e., an active pharmaceutical ingredient) at or near the predetermined target site. In other words, prodrugs are inactive compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction (52-53).

The phrase "hydroxy-protecting group" refers to any suitable group, such as tert-butyloxy-carbonyl (t-BOC) and t-butyl-dimethyl-silyl (TBS). Other hydroxy protecting groups contemplated are known in the art (54).

The pharmaceutically suitable oral carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, the oral dosage form includes capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), osmotic, and the like.

The oral dosage form composition contains an active pharmaceutical ingredient and may contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use.

Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

"Pharmaceutically suitable inhalation carrier systems" include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

As used herein, a transdermal dosage form includes, but is not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

An effective dose of a compound contemplated herein will generally be any amount that has a beneficial physiologically effect on a patient. In one embodiment, an EC50 value for a patient of a compound contemplated herein may range from 30 µM (±10%) to 600 µM (±10%) or about 4-10 fold (±1-2 fold) of an effective in vitro value in a physiologically relevant model.

EXAMPLES

Example 1

Synthesis of Mito-Apocynin and Mito-Apocyninacetate

Figure 3:
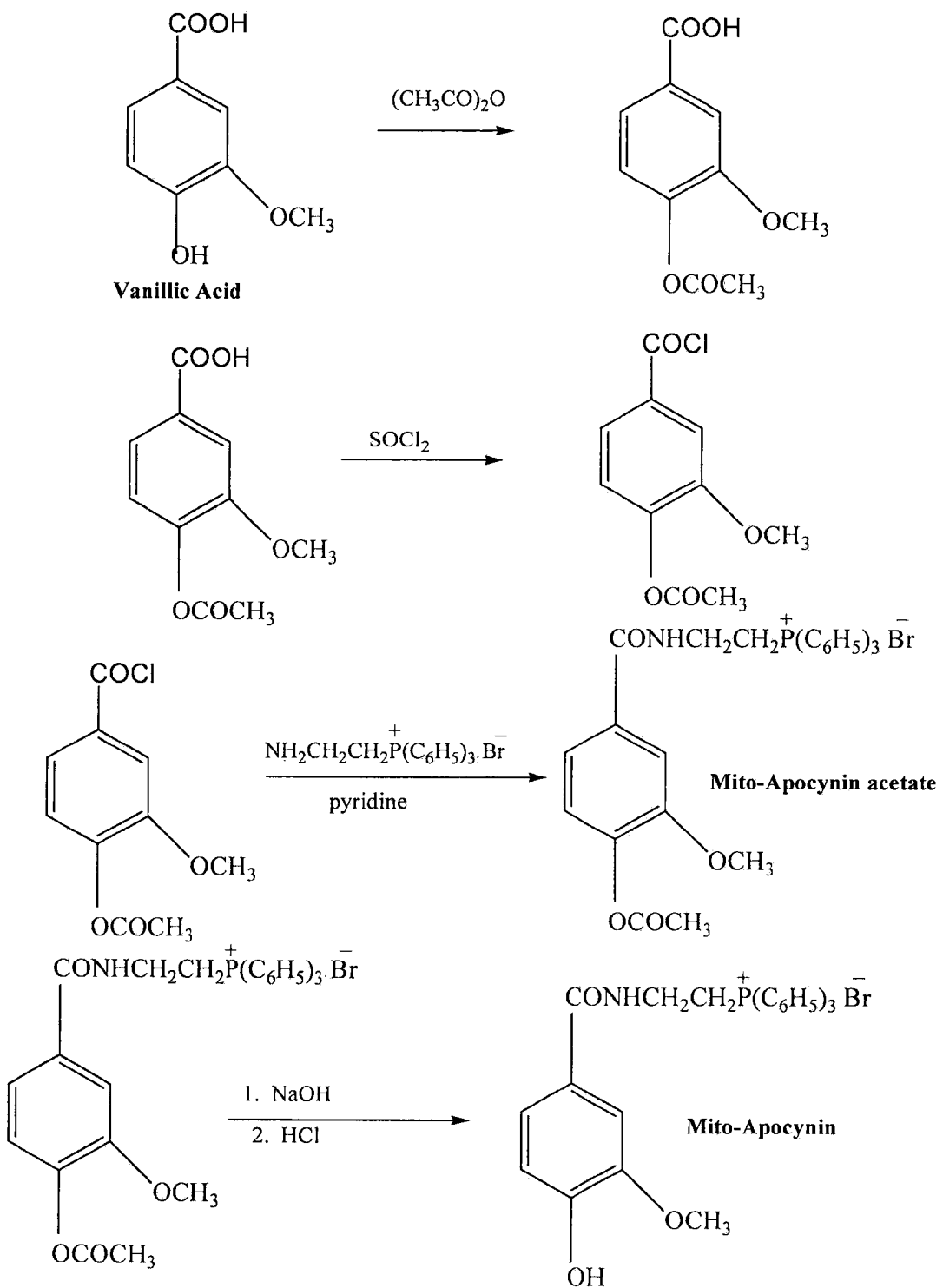
FIG. 3 illustrates a series of synthesis reactions of Mito-Apocyninacetate and Mito-Apocynin.

The synthesis of Mito-apocynin and Mito-apocyninacetate involves the coupling of acetylvanillic acid chloride with triphenyl-2-aminoethylphosphoniumbromide, resulting in mito-apocyninacetate that is hydrolyzed to mito-apocynin. The synthetic schemes for Mito-apocynin and Mito-apocyninacetate are depicted in FIG. 3.

Vanillic acid (10 g) was heated at 60° C. for one hour with 10 ml acetic anhydride containing 2-3 drops of concentrated sulfuric acid. The hot mixture was poured into 100 ml ice cold water and extracted with 2×5 ml ether. The ether extract was dried and solvent removed, and finally dried on a vacuum line to obtain quantitative yield of acetyl vanillic acid as a dull white solid.

The above compound was suspended in 50 ml dry benzene and 10 ml of thionyl chloride was added. The mixture was refluxed for one hour. The solvent was removed from the solution by rotary evaporation, 20 ml more benzene was added, and again the solvent removed. Finally, the residue was dried on a vacuum line to obtain a light brown semisolid. This moisture-sensitive acid chloride was used in the coupling reaction.

Triphenylphosphine (13 g, 0.05 mole) and 2-bromoethylamine hydrobromide (10.25 g, 0.05 mole) were stirred under reflux in 100 ml of n-propanol for 72 hr in nitrogen atmosphere. The white solid formed was filtered after cooling. The residue was washed repeatedly with dry ether and dried on a vacuum line. The product was dissolved in 50 ml water and filtered. Dilute ammonia was added to the solution until the pH reached 9.0. The free amine was extracted with dichloromethane (3×50 ml). The organic layer was collected and dried over anhydrous magnesium sulfate and solvent removed, and finally dried on a vacuum line. Purity was ascertained by HPLC and LC/MS (mass=306).

2-aminoethyl triphenylphosphonium bromide (3.86 g, 0.01 mole) was dissolved in 50 ml dry dichloromethane, and to this, 2 g of pyridine was added. This solution was kept stirred in an ice bath. To the stirred solution, a solution of acetylvanillic acid chloride (2.28 g, 0.01 mole) in 20 ml dichloromethane was added in drops over a half hour period.

The solution was then stirred overnight at room temperature. The solution was shaken with a saturated solution of sodium bicarbonate to remove any acid and then shaken with 0.1 M hydrochloric acid to remove any basic compounds. The organic layer was collected, dried, and solvent removed to obtain a light brown semisolid. This intermediate product, Mito-Apocyninacetate, was isolated and purified by dissolution in dichloromethane and precipitation from ether several times. Purity was confirmed by HPLC and LC/MS (mass=498).

The protective acetyl group was removed by dissolving the product in 25 ml methanol and stirring at room temperature with 5 ml aqueous solution of 1 g NaOH for 1 hr. The deacetylated compound was recovered by acidifying with dilute HCl until pH was 3.0 and extracting with dichloromethane. Removal of solvent produced a semisolid, which was purified by dissolving the semisolid in 10 ml dichloromethane and adding the solution to 100 ml of dry ether while being stirred. The precipitated product was collected by decanting, and the ether was removed completely. This process of purification by precipitation was repeated two more times, and the product finally dried on a vacuum line to obtain a dull-white powder. Purity of mito-apocynin was ascertained by HPLC and LC/MS (mass=456). The final yield was 50%.

Example 2

Neuroprotective Effects of Mitochondria-Targeted Apocynin Analog in a Subchronic MPTP Mouse Model Apocynin and apocynin analogues exhibit potent neuroprotective properties (55). Administration of apocynin (300 mg/kg) markedly enhanced the lifespan of G93A mice, a well-known rodent model of ALS (5 and 55).

Although apocynin and related analogues (for example, vanillin) inhibit NADPH oxidase activity (thereby quenching superoxide formation), these compounds also exhibit antioxidant properties (3). The triphenylphosphonium-conjugated apocynin analogue, Mito-apocynin, acts as a potent mitochondrial targeted antioxidant (MTA). The nigrostriative dopaminergic neurons undergo destruction in a slow and progressive manner in idiopathic PD. In order to mimic this condition in a preclinical mouse model, a subchronic MPTP mouse model was developed. The mouse model used here was similar to that used in Example 3 below.

Figure 4:
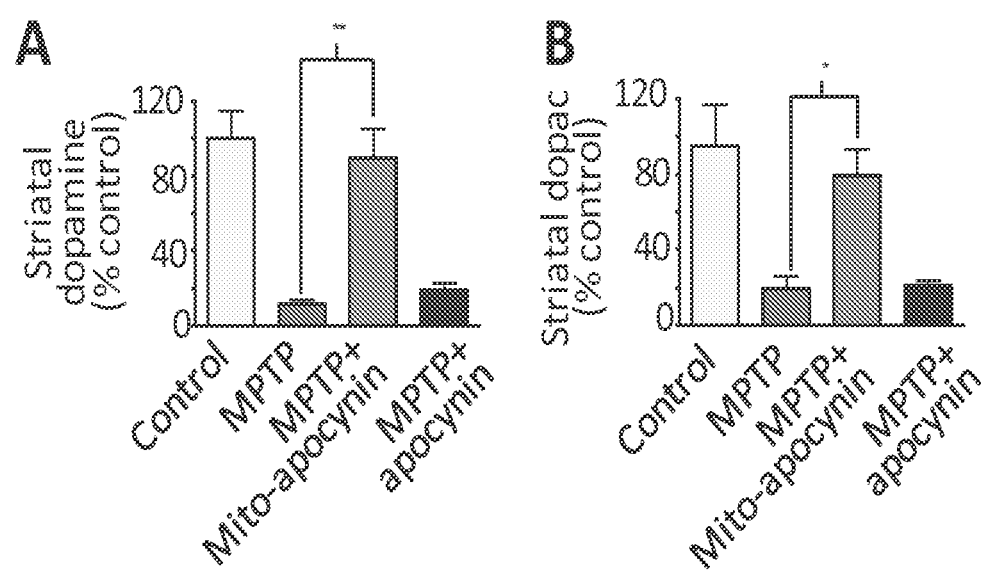
FIG. 4 shows two bar graphs of the comparative effects of Mito-apocynin and apocynin on striatal dopamine (A) and dopac (B) levels in a subchronic MPTP mouse model (n=5-7)

Mice were treated with Mito-apocynin (3 mg/kg, oral gavage) for 1 day followed by subchronic MPTP (20 mg/kg, i.p.) administration for 5 days. Animals were sacrificed 7 days after the last dose of MPTP (Mito-apocynin was administered during the 7 days). Striatal neurotransmitters (dopamine, dopac) were analyzed by HPLC-EC. Similar experiments were performed with apocynin (20 mg/kg, oral gavage; lower doses were also tested but not effective). As shown in FIGS. 4A and 4B, Mito-apocynin (but not apocynin) almost completely protected against subchronic MPTP-induced depletion of striatal dopamine and dopac levels at the concentration used in these experiments.

As PD onset is characterized by striatal dopamine deficiency, the existing therapy involves the administration of L-dopa to PD patients. However, L-dopa therapy is associated with toxic side effects, including hepatotoxicity and dyskinesia. The instant invention demonstrates that mitigating mitochondrial damage using MTAs is beneficial by restoring dopamine levels in the striatum. The instant MTAs mitigate dopamine loss in the animal model of PD. Further, the use of MTAs may mitigate cytotoxicity associated with L-dopa therapy.

Example 3

Evaluation of Anti-Neuroinflammatory Effect of Diapocynin in MPTP Mouse Model of Parkinson's Disease Animals and Treatment.

Six- to 8-week-old C57BL/6 mice weighing 24 to 28 g were housed in standard conditions of constant temperature ($22\pm1°$ C.), humidity (relative, 30%), and a 12-h light/dark cycle. Mice were allowed free access to food and water. Use of the animals and protocol procedures were approved and supervised by the Committee on Animal Care at Iowa State University (Ames, Iowa). For neurodegeneration studies, mice either received diapocynin (300 mg/kg dose) by oral gavage for 1 day (pre-treatment before MPTP administration), 5 days (co-treatment with MPTP), or 7 days (post-treatment after MPTP).

For checking inflammatory and oxidative stress markers, mice were gavaged diapocynin (300 mg/kg dose) 1 day before MPTP treatment (pre-treatment) and continued for another 4 days of co-treatment with MPTP. In the sub-acute MPTP regimen, MPTP (25 mg/kg) was injected intraperitoneally once per day from day 2 to day 7. Control mice received saline at the same dosage.

HPLC Analysis Striatal Dopamine and its Metabolites Levels.

Striatal dopamine (DA), DOPAC and HVA levels were quantified by high-performance liquid chromatography (HPLC) with electrochemical detection. Samples were prepared and quantified as described previously (48, 56). In brief, 7 days after MPTP injection mice were sacrificed, striata were collected and stored at $-80°$ C. On the day of analysis, neurotransmitters from striatal tissues were extracted using an antioxidant extraction solution (0.1 M perchloric acid containing 0.05% $Na_2EDTA$ and 0.1% $Na_2S_2O_5$) and isoproterenol (as an internal standard). The extracts were filtered in 0.22 µm spin tubes, and 20 µl of the samples were loaded for analysis. DA, DOPAC and HVA were separated isocratically on a reversed-phase column with a flow rate of 0.6 ml/min. An HPLC system with an automatic sampler equipped with refrigerated temperature control (model 542; ESA, Inc., Bedford, Mass.) was used for HPLC analysis. The electrochemical detection system consisted of a Coulochem (model 5100A, ESA, Inc.) with a microanalysis cell (model 5014A, ESA, Inc.) and a guard cell (model 5020, ESA, Inc.). The data acquisition and analysis were performed using the EZStart HPLC Software (ESA, Inc.).

Immunohistochemistry.

Four days after MPTP treatment, mice were perfused with 4% paraformaldehyde (PFA) and post-fixed with PFA and 30% sucrose, respectively. Next, fixed brains were cut into 30 µm sections and kept in 30% sucrose-ethylene glycol solutions at $-20°$ C. On the day of staining, sections were rinsed with phosphate-buffered saline (PBS) and incubated with different primary antibodies, including anti-IBA-1 (DAKO, Carpinteria, Calif.), anti-GFAP (Millipore, Billerica, Mass.), anti-iNOS (Santa Cruz Biotechnology, Santa Cruz, Calif.), anti-3NT (Millipore), anti-4HNE (R&D Systems, Minneapolis, Minn.) and anti-gp91phox (Santa Cruz Biotechnology) for overnight at $4°$ C. Appropriate secondary antibodies (Alexa Fluor 488, 594, or 555 from Invitrogen, Carlsbad, Calif.) were used followed by incubation with 10 µg/ml Hoechst 33342 for 5 min at room temperature to stain the nucleus. Sections were viewed under a Nikon inverted fluorescence microscope (model TE-2000U; Nikon, Tokyo, Japan). Images were captured with a SPOT digital camera (Diagnostic Instruments, Inc., Sterling Heights, Mich.).

DAB Immunostaining.

DAB immunostaining was performed in striatal and substantia nigra sections as described previously (57). In brief, 1 day or 7 days after final dosing of MPTP, mice were sacrificed and perfused with 4% PFA and post-fixed with PFA and 30% sucrose, respectively. Next, fixed brains were cut into 30 μm sections and kept in 30% sucrose-ethylene glycol solutions at −20° C. On the day of staining, sections were rinsed with PBS and incubated with either anti-TH (rabbit anti-mouse, 1:1800; Calbiochem, Gibstown, N.J.), anti-IBA-1 (goat anti-mouse, 1:1000; Dako), anti-GFAP (mouse anti-mouse, 1:1000; Millipore, Billerica, Mass.), or anti-gp91phox (mouse anti-mouse, 1:500; Santa Cruz Biotechnology) overnight at 4° C. Next, sections were incubated in biotinylated anti-rabbit, -goat, or -mouse secondary antibodies for 1.5 hr at room temperature. The sections were then incubated with avidin peroxidase (Vectastatin ABC Elite kit; Vector Labs, Burlingame, Calif.) for 30 min at room temperature. Immunolabeling was observed using diaminobenzidine (DAB), which yielded a brown stain.

Western Blot.

Mice were sacrificed 4 days or 7 days after MPTP treatment and substantia nigra tissue was dissected out. Brain lysates containing equal amounts of protein were loaded in each lane and separated on a 10 to 12% SDS polyacrylamide gel, as described previously (48). After the separation, proteins were transferred to a nitrocellulose membrane and non-specific binding sites were blocked by treating with Li-Cor Odyssey blocking buffer (Li-Cor Biosciences, Lincoln, Nebr.). The membranes were then incubated with different primary antibodies including anti-TH (Millipore), anti-iNOS (Calbiochem), anti-3NT (Millipore) and anti-4HNE (R&D Systems). Next, membranes were incubated with Alexa Fluor 680 goat anti-mouse or Alexa Fluor 680 donkey anti-goat (Invitrogen) or IR dye 800 donkey anti-rabbit secondary antibodies (Rockland Immunochemicals, Gilbertsville, Pa.). To confirm equal protein loading, blots were reprobed with a β-actin antibody (1:5000 dilution). Western blot images were captured with a Li-Cor Odyssey machine (Li-COR Biosciences).

FLUORO-JADE B® and Tyrosine Hydroxylase Double Labeling.

FLUORO-JADE B® and tyrosine hydroxylase (TH) double-labeling was performed in substantia nigra sections, as described previously (58). In brief, 7 days after the final MPTP injection, mice were sacrificed and perfused with 4% PFA and post-fixed with PFA and 30% sucrose, respectively. Fixed brains were cut into 30 μm sections and kept in 30% sucrose-ethylene glycol solutions at −20° C. On the day of staining, sections were rinsed with PBS and incubated with anti-TH antibody (Millipore, mouse monoclonal, dilution 1;1600) followed by Alexa Fluor 568 donkey anti-mouse secondary antibody (Invitrogen). FLUORO-JADE B® staining was done on the same sections by modified FLUORO-JADE B® stain protocol including incubation of 0.06% potassium permanganate for 2 min and 0.0002% FLUORO-JADE B® stain for 5 min. Sections were viewed under a Nikon inverted fluorescence microscope (model TE-2000U). Images were captured with a SPOT digital camera (Diagnostic Instruments, Inc.).

Behavioral Measurements.

Two types of behavioral tests were performed including an Open Field experiment for testing locomotor activities and a Rotarod experiment to test coordination of movement of mice after MPTP and diapocynin treatment (48, 56). An Open Field activity monitor (model RXYZCM-16; AccuScan, Columbus, Ohio) was used to measure the spontaneous activity of mice. The activity chamber was 40×40×30.5 cm, made of clear PLEXIGLAS® and covered with a PLEXIGLAS® lid with holes for ventilation. Infrared monitoring sensors were located every 2.54 cm along the perimeter (16 infrared beams along each side) and 2.5 cm above the floor. Two additional sets of 16 sensors were located 8.0 cm above the floor on opposite sides. Data were collected and analyzed by a Versa-Max Analyzer (model CDA-8, AccuScan). Before treatment, mice were placed inside the infrared monitor for 10 min daily and 5 min daily for 3 consecutive days to train them. Five days after the last MPTP injection Open Field and Rotarod experiments were conducted. Locomotor activities were presented as horizontal movement and vertical movement for 10 min test sessions. For Rotarod experiments, a 20 rpm speed was used. Mice were given a 5-7 min rest interval to eliminate stress and fatigue.

Example 3

Results

Diapocynin Inhibits the Glial Activation in Substantia Nigra of MPTP-Induced Mouse Model of PD.

Figure 5:
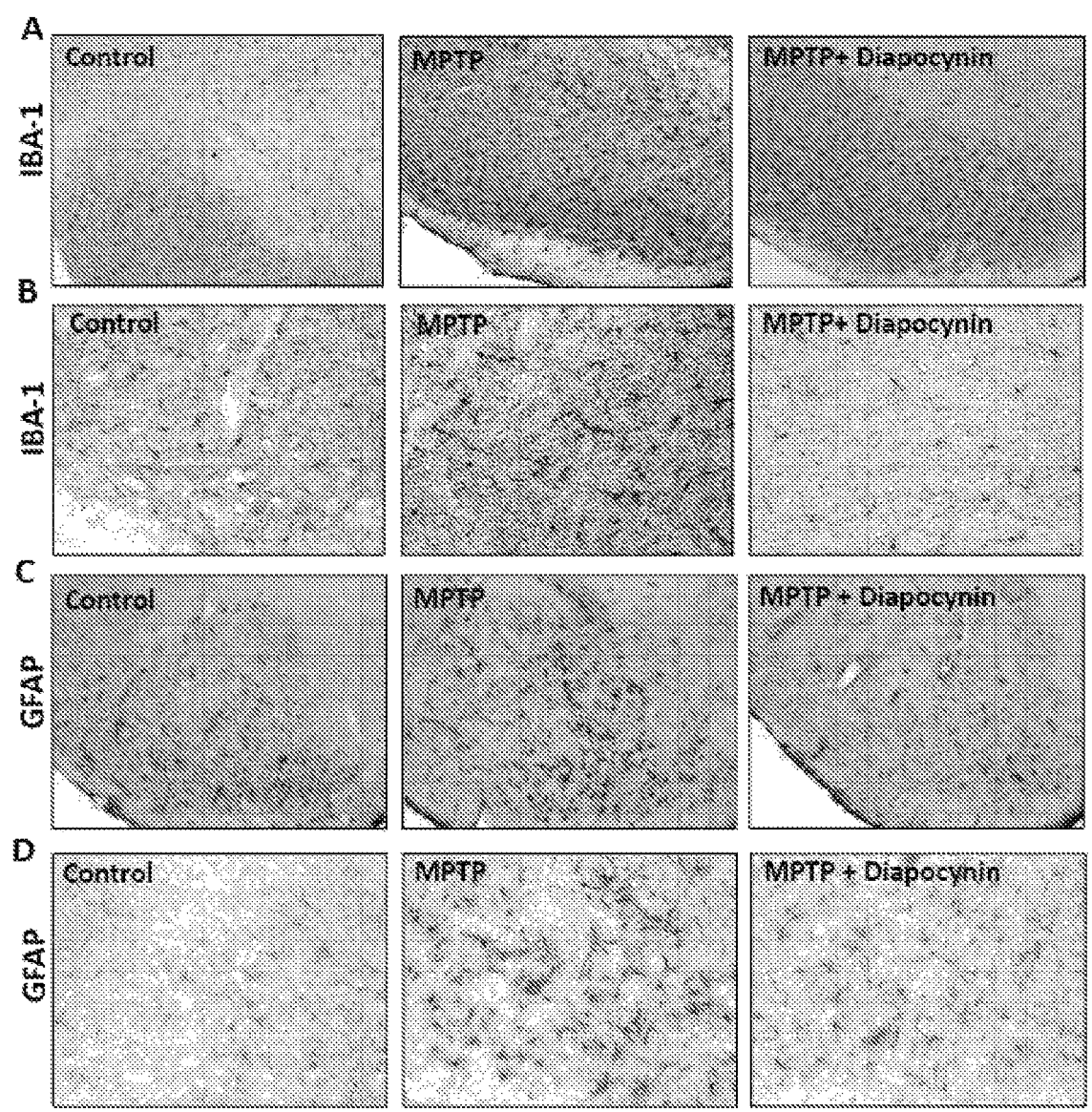
FIG. 5 shows the protective effects of diapocynin against neuroinflammation in an MPTP mouse model of PD as measured by microglial activation (IBA-1 expression) and astroglial activation (GFAP) in the substantia nigra. Substantia nigra tissue sections were immunolabeled for IBA-1 (panel A, 10× magnification and panel B, 30× magnification) and GFAP (panel C, 10× magnification and panel D, 30× magnification)

Recent research demonstrates that activation of glial cells is a pathological hallmark in Parkinson's disease (PD) and other neurodegenerative disorders (56-57 and 59-60). Consistent with these findings, increased expression of IBA-1 (marker of microglia) and GFAP (marker of astrocytes) were observed in substantia nigra of MPTP-treated mice (FIG. 5, panels A-D). Higher magnification (FIG. 5, panels B and D) showed increased microgliosis (amoeboid shape and increased morphology) and astrogliosis (increased expression and increased morphology) with MPTP treatment. Treatment of MPTP-intoxicated mice with diapocynin led to the inhibition of IBA-1 and GFAP protein expression in substantia nigra (FIG. 5, panels A-D). These results indicate that diapocynin reduces increased activation of glial cells in MPTP-treated mice.

Diapocynin Attenuates MPTP-Induced Expression of gp91phox.

Figure 6:
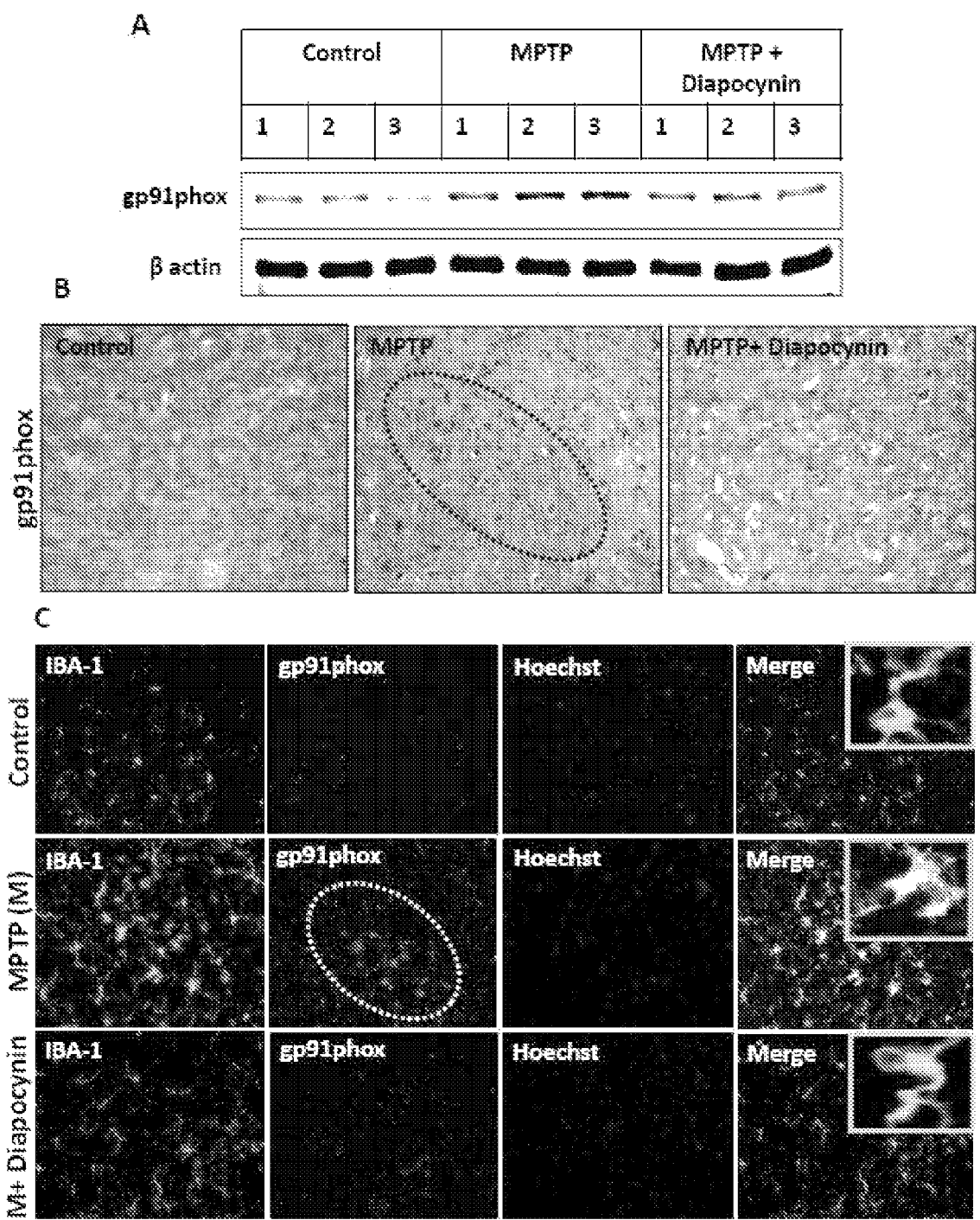
FIG. 6 shows expression of gp91phox (a marker of NADPH oxidase-mediated inflammatory response) in substantia nigra is attenuated by diapocynin in MPTP-treated mice. Substantia nigra tissue was processed for Western blot analysis to check expression levels of gp91phox (panel A), or sectioned and immunolabeled for gp91phox by DAB-immunostaining (panel B, 10× magnification) and double-labeled with gp91phox and IBA-1 (panel C, 30× magnification)

Oxidative stress and neuroinflammation have been implicated in the pathogenesis of PD. Accordingly, increased expression of NADPH oxidase in human PD brain and in MPTP-induced mouse midbrain have been demonstrated (61). Similarly, here increased expression of gp91phox was found in substantia nigra tissue of MPTP-treated mice by Western blot analysis (FIG. 6, panel A) and by DAB-immunostaining (FIG. 6, panel B). However, diapocynin treatment attenuated MPTP-induced expression of gp91phox in substantia nigra (FIG. 6, panels A & B). DAB-immunostaining of gp91phox (FIG. 6, panel B) in MPTP-treated cells shows robust cells, with thick, shorter ramification, expressing gp91phox. In contrast, the control and MPTP- and diapocynin-treated sections demonstrated mild immunoreactivity. Double-labeling of IBA-1 and gp91phox demonstrated that gp91phox colocalized with IBA-1 positive cells in MPTP treated mice, whereas no colocalization was found in mice treated with MPTP and diapocynin (FIG. 6, panel C). These results show that diapocynin blocks MPTP-induced gp91phox activation in microglial cells.

Diapocynin Inhibits MPTP-Induced Expression of 3-Nitrotyrosine.

Figure 7:
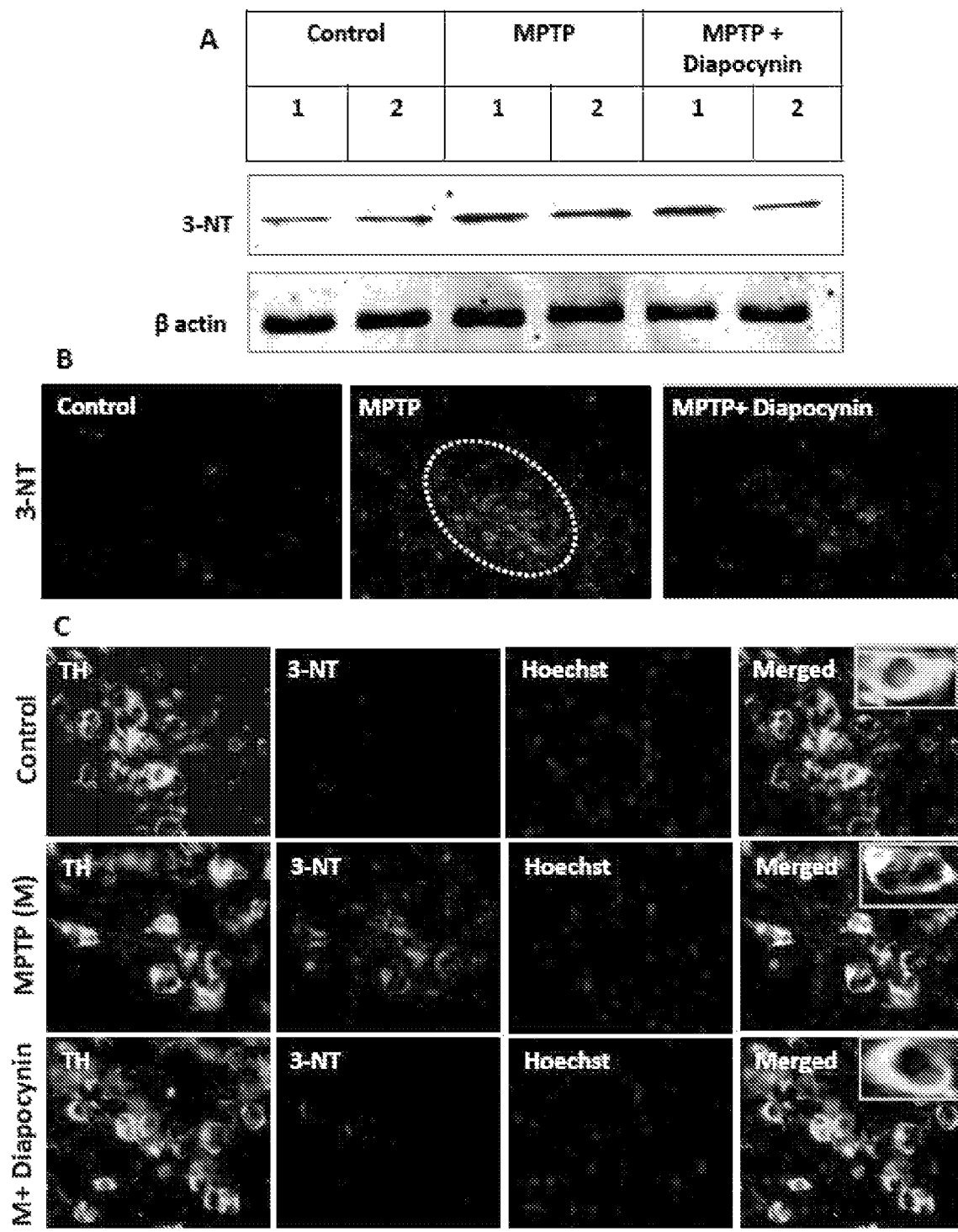
FIG. 7 shows that diapocynin attenuates 3-nitrotyrosine (3-NT: a marker of iNOS/NOS2 activation) expression induced by MPTP in the substantia nigra of mice. Substantia nigra tissue was processed for Western blot analysis to check expression levels of 3-nitrotyrosine (panel A) or sectioned and immunolabeled for 3-nitrytyrosine (3-NT) by DAB-immunostaining (panel B, 10× magnification) and double-labeled with 3-NT and IBA-1 (panel C, 60× magnification)

Protein nitration due to oxidative and nitrative stress has been linked to the pathogenesis of PD and observed in the MPTP model of PD. In oxidative stress conditions, superoxide reacts with nitric oxide and forms peroxynitrite, a potent oxidant that selectively nitrates tyrosine residues and generates 3-nitrotyrosine (3-NT), which has been widely used as a marker of nitric oxide-dependent oxidative stress. Here, increased expression of 3-NT in substantia nigra of MPTP-treated mice was found (FIG. 7, panels A and B). Moreover, diapocynin attenuated MPTP-induced expression of 3-NT in substantia nigra (FIG. 7, panels A and B).

Next, we speculated that dopaminergic neurons also express 3-NT. Double-labeling immunostaining of tyrosine hydroxylase (TH, a marker for dopaminergic neurons) and 3-NT revealed that 3-NT colocalized mainly with TH-positive neurons in substantia nigra regions of MPTP-treated mice. However, very few TH positive cells colocalized with 3-NT in MPTP-treated mice that also received diapocynin (FIG. 7, panel C). The reduction of 3-NT formation indicates that diapocynin prevents protein oxidation induced by MPTP in dopaminergic neurons of the substantia nigra.

Diapocynin Reduced MPTP-Induced 4-Hydroxynonenol Production in Substantia Nigra.

Figure 8:
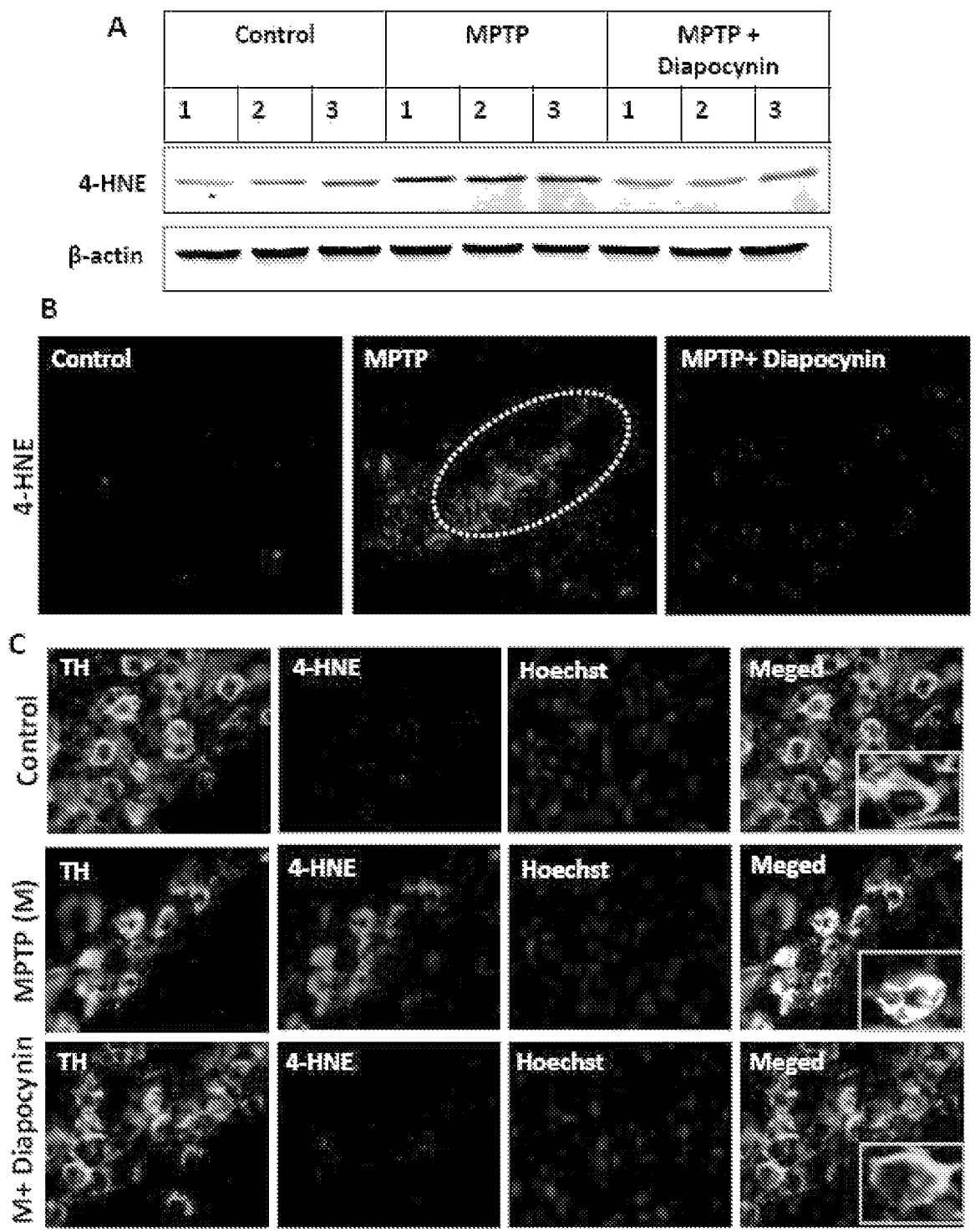
FIG. 8 shows that diapocynin inhibits the level of 4-HNE (marker of oxidative damage) in substantia nigra of MPTP-intoxicated mice. Substantia nigra tissue was processed for Western blot analysis to check expression level of 4-hydroxynonenol (4-HNE) (panel A), or sectioned and immunolabeled for 4-HNE (panel B, 10× magnification) and double-labeled with 4-HNE and IBA-1 (panel C, 60× magnification)

4-hydroxynonenol (4-HNE) is a major product of unsaturated aldehyde formed during lipid peroxidation and is widely used as a marker of membrane lipid peroxidation induced by hydroxyl radicals (62). It has been found that 4-HNE mediates neuronal apoptosis in the presence of oxidative stress (63). Previous reports also have shown that 4-HNE is a good marker of oxidative damage in PD (64). Here, increased expression of 4-HNE was demonstrated in the substantia nigra of MPTP-treated mice by Western blot and immunostaining (FIG. 8, panels A and B). However, diapocynin attenuated the MPTP-induced increase in expression of 4-HNE in substantia nigra (FIG. 8, panels A and B).

Double-label immunostaining also demonstrated that TH-positive dopaminergic neurons strongly expressed 4-HNE in substantia nigra regions of MPTP-treated mice. In contrast, MPTP- and diapocynin-treated mice showed very few colocalized cells of TH and 4-HNE in substantia nigra (FIG. 8, panel C). These results indicate that diapocynin suppresses the expression of 4-HNE in dopaminergic neurons in substantia nigra of MPTP-intoxicated mice.

Diapocynin Inhibits the Expression of Inducible Nitric Oxide Synthase in the Substantia Nigra of MPTP-Treated Mice.

Figure 9:
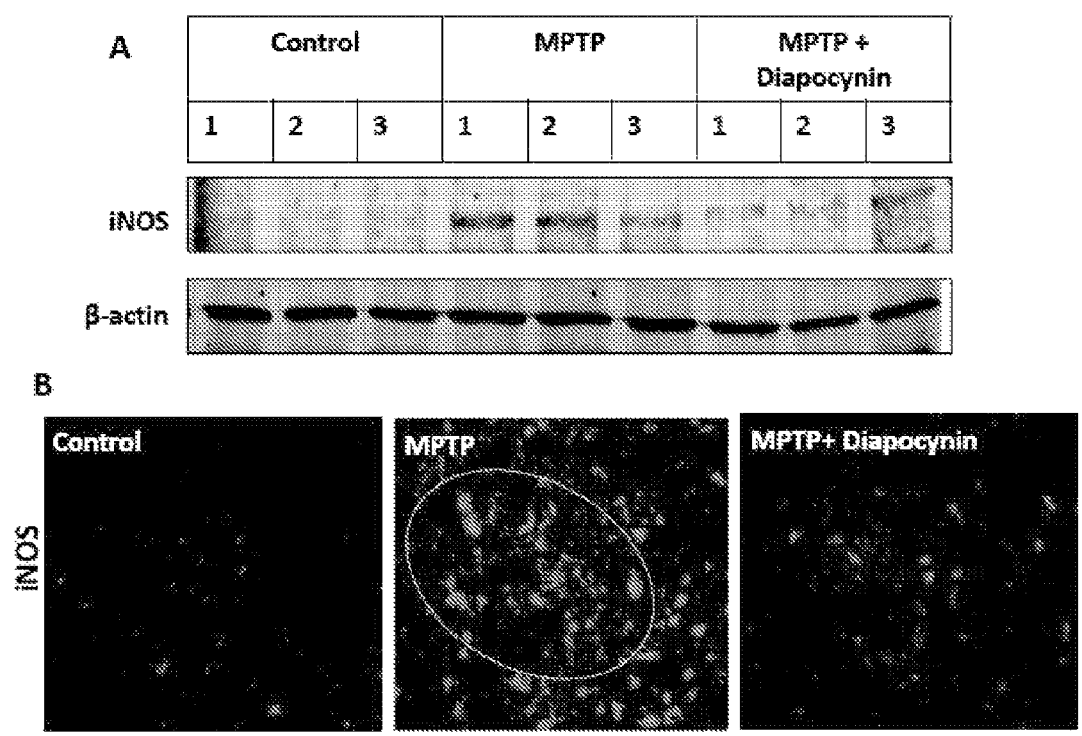
FIG. 9 shows that increased expression of iNOS in the substantia nigra by MPTP is attenuated by oral treatment of diapocynin. Substantia nigra tissue was processed for Western blot analysis to check expression level of inducible nitric oxide synthase (iNOS) (panel A) or sectioned and immunolabeled for iNOS (panel B, 30× magnification)
Figure 10:
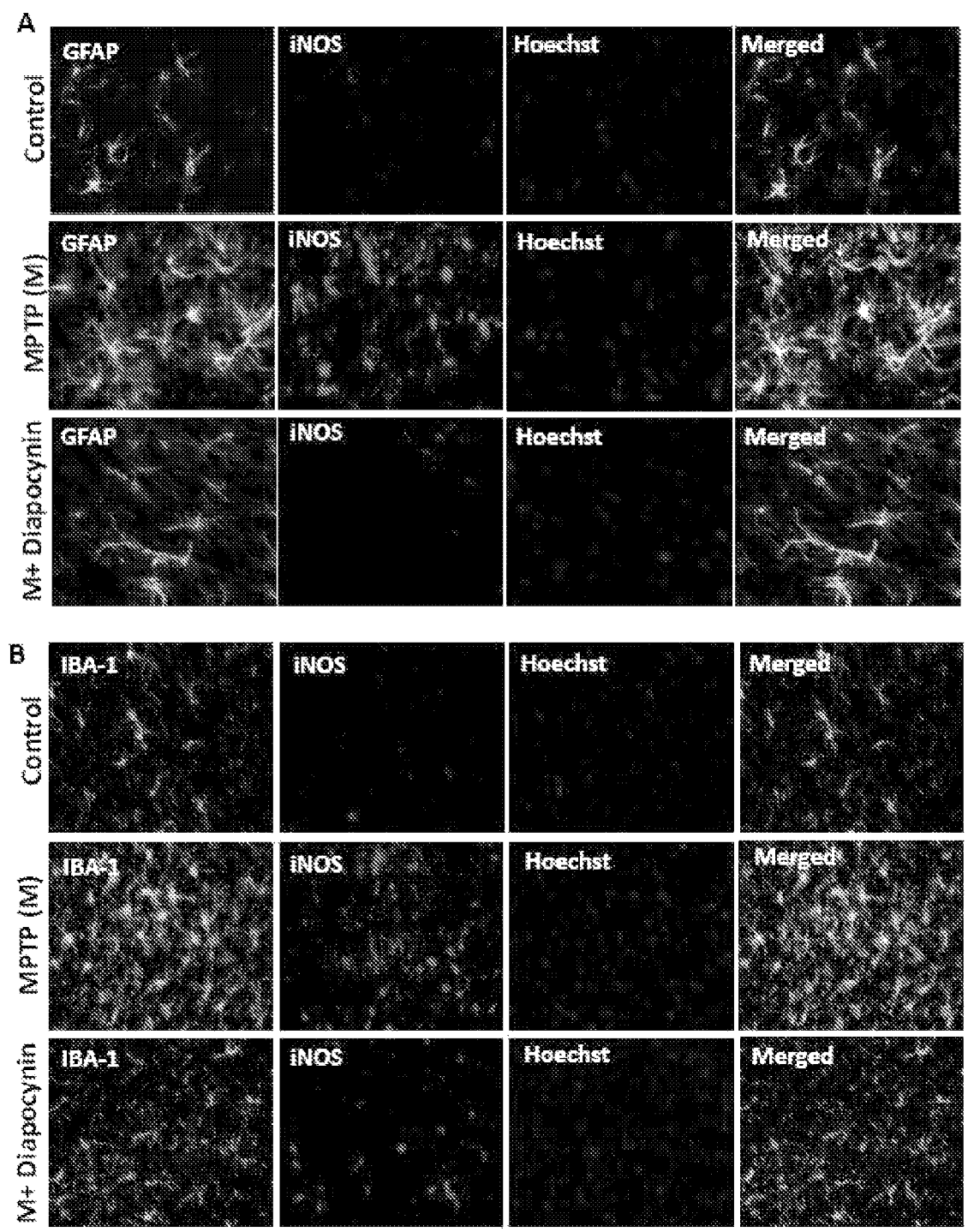
FIG. 10 shows that MPTP-induced glial cell expression in substantia nigra is inhibited by diapocynin. Substantia nigra tissue sections were double-labeled for IBA-1 and iNOS (panel A, 30× magnification) and GFAP and iNOS (panel B, 30× magnification)

Various researchers have demonstrated the role of inflammation associated with PD neurodegeneration in animal models (65-66). Here, the expression level of inducible nitric oxide synthase (iNOS/NOS2) was measured in the substantia nigra of mice by Western blot and immunostaining to assess MPTP-induced inflammation. An increased expression level of iNOS was observed in the substantia nigra of MPTP-treated mice when compared to saline-treated control mice (FIG. 9, panels A and B). Further, increased iNOS colocalization with IBA-1 positive microglia and GFAP-positive astrocytes were observed in MPTP-treated mice (FIG. 10, panels A and B).

However, a marked decrease in staining of iNOS in MPTP-treated mice that also received diapocynin was observed (FIG. 9, panels A and B). Further, and consistent with our findings from FIG. 5 that show that diapocynin attenuated MPTP-induced expression of IBA-1 and GFAP, very few colocalized cells of either iNOS and IBA-1 or iNOS and GFAP were observed in the substantia nigra of MPTP-treated mice that also received diapocynin (FIG. 10, panels A and B). These results demonstrate the effectiveness of diapocynin as an anti-inflammatory agent against MPTP-induced inflammatory reactions and its potential as a neuroprotective anti-inflammatory agent in patients with PD.

Diapocynin Improves Locomotor Activities in MPTP-Injected Mice.

Figure 11:
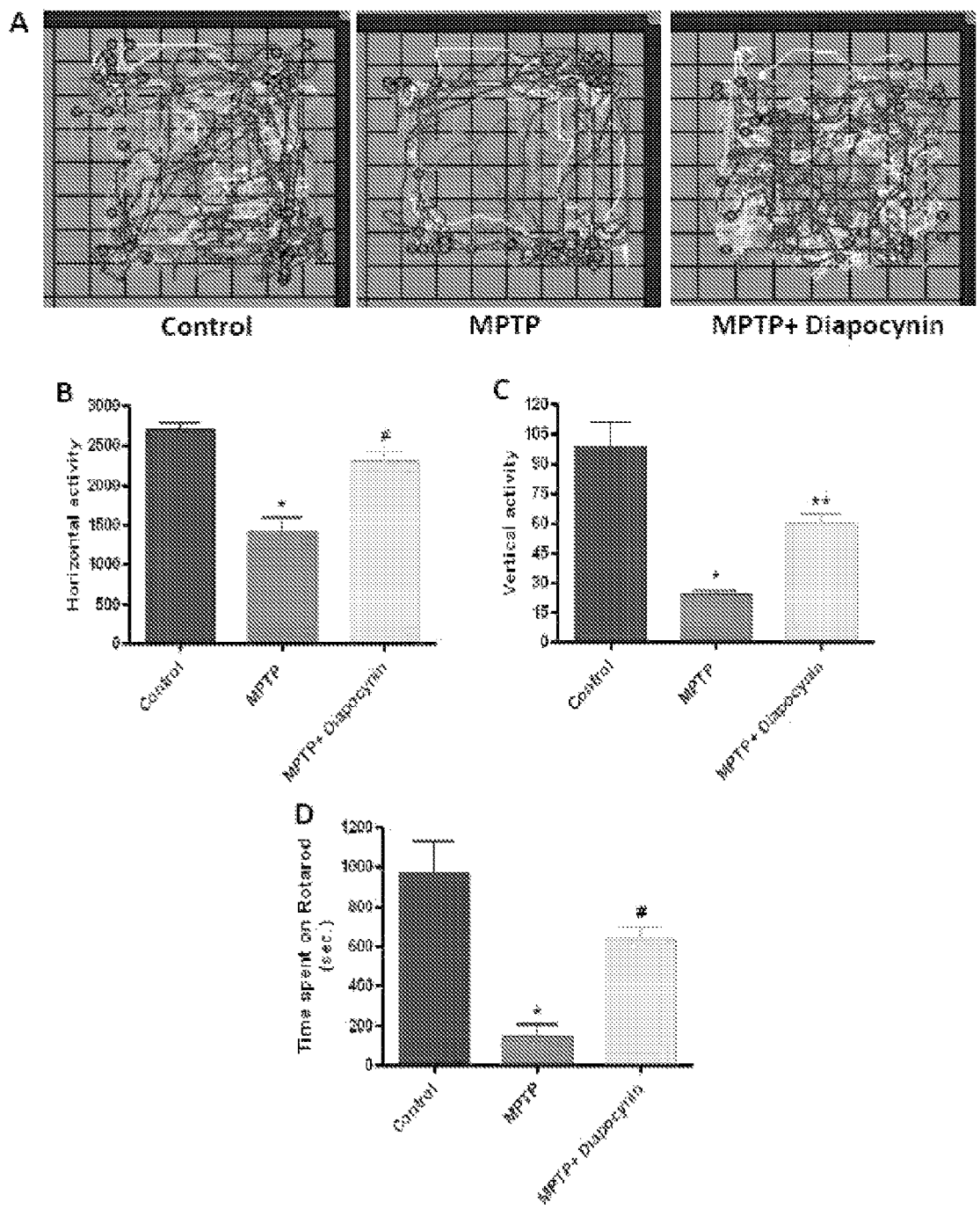
FIG. 11 shows that diapocynin improves motor function in MPTP-intoxicated mice. Locomotor activities were measured using VersaMax analyzer and rotarod [moving track of mice (Versaplot) (panel A); horizontal activity (panel B); vertical activity (panel C); time spent on rotarod (panel D)]. Data are means+SEM, n=10 per group. *=p<0.001 compared to control; #=p<0.01 compared to MPTP treatment; **=p<0.05 compared to MPTP treatment.

In order to assess the effectiveness of diapocynin against motor deficits induced by MPTP, locomotor activities were measured in control, MPTP-treated, and MPTP- and diapocynin-treated mice. Versa Plot representative maps of control, MPTP, and MPTP- and diapocynin-treated mice are mice are seen in FIG. 11, panel A. Horizontal activities were reduced by nearly 50% and vertical activities were reduced by greater than 75% reduction in MPTP-treated mice compared to controls (FIG. 11, panels B and C). Notably, MPTP- and diapocynin-treated mice demonstrated significantly improved performances in horizontal and vertical activities (FIG. 11, panels A, B, and C).

At a 20 rpm speed, MPTP-intoxicated mice showed a greater than 75% decrease in time spent on Rotarod compared to control mice (FIG. 11, panel D). However, MPTP- and diapocynin-treated mice showed less than a 25% decrease in time spent on Rotarod when compared to control mice (FIG. 11, panel D). Together, these findings demonstrate that diapocynin is capable of inhibiting the behavioral deficits caused by the neurotoxin MPTP, and further indicate the potential of diapocynin for improving motor deficits associated with neurodegeneration.

Diapocynin Protects Against the Neurotransmitter Deficits in an MPTP-Induced Animal Model of PD.

Figure 12:
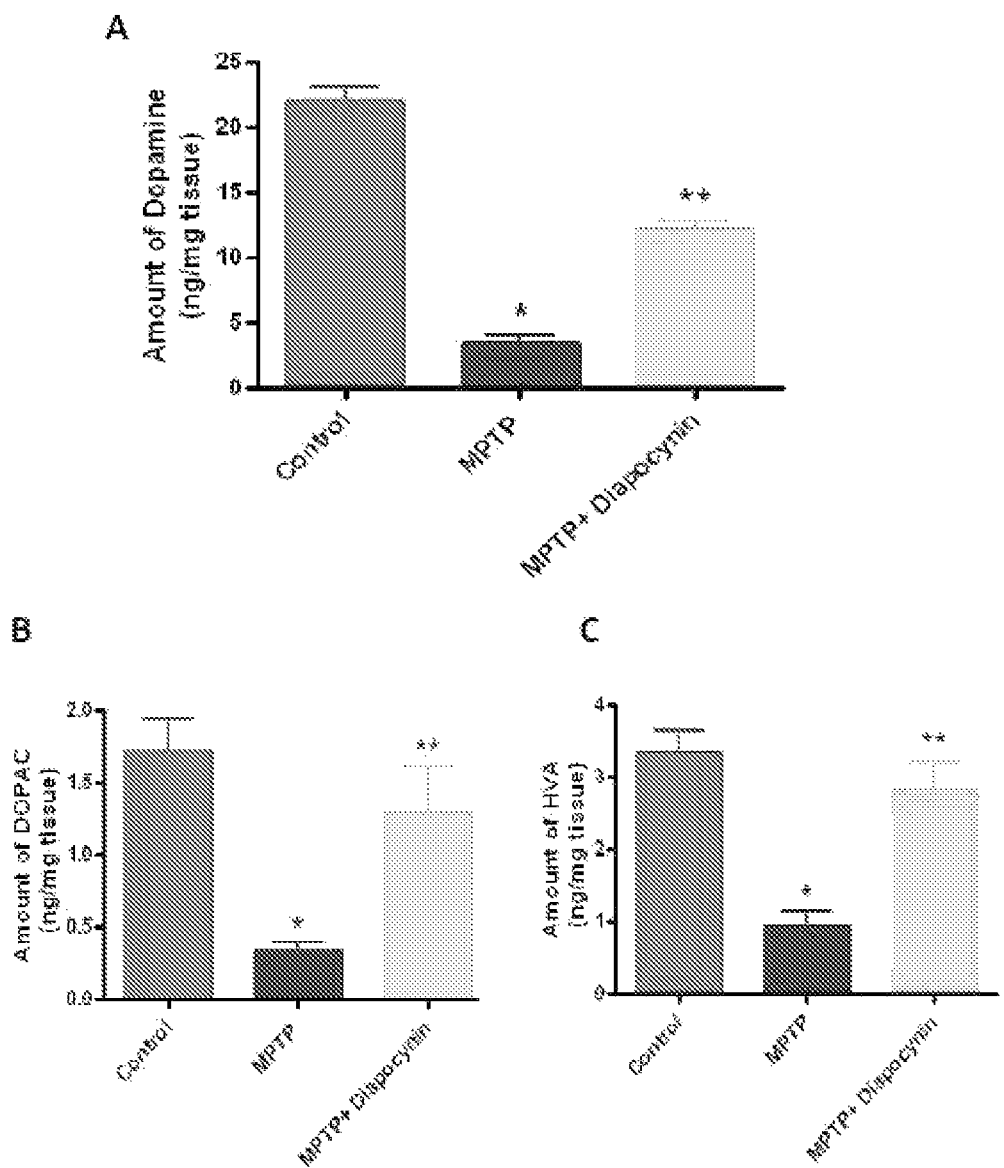
FIG. 12 shows that diapocynin prevents MPTP-induced loss of dopamine and its metabolites in mice striatum. Dopamine (panel A), DOPAC (panel B) and HVA (panel C) were measured from the striatum by HPLC. Data are means+SEM, n=10 per group. *=p<0.001 compared to control; **=p<0.01 compared to MPTP treatment.

As we found a protective effect by diapocynin in MPTP-induced behavioral deficits, we checked whether diapocynin could protect against neurochemical deficits caused by MPTP. MPTP intoxication led to a greater than 78% reduction of dopamine levels, whereas MPTP- and diapocynin-treated mice showed a less than 40% decrease of dopamine levels in striatum (FIG. 12, panel A). We also found a significant decrease of striatal DOPAC and HVA levels with MPTP-intoxicated mice, whereas MPTP- and diapocynin-treated mice showed significant preservation of striatal DOPAC and HVA levels (FIG. 12, panels B and C). These results demonstrate the neuroprotective characteristic of diapocynin against decreased dopamine levels associated with MPTP toxicity. Moreover, these results highlight the protective effects of diapocynin against neurochemical deficits associated with inflammatory diseases, such as PD.

Diapocynin Protects the Nigrostriatum Against MPTP Toxicity.

Figure 13:
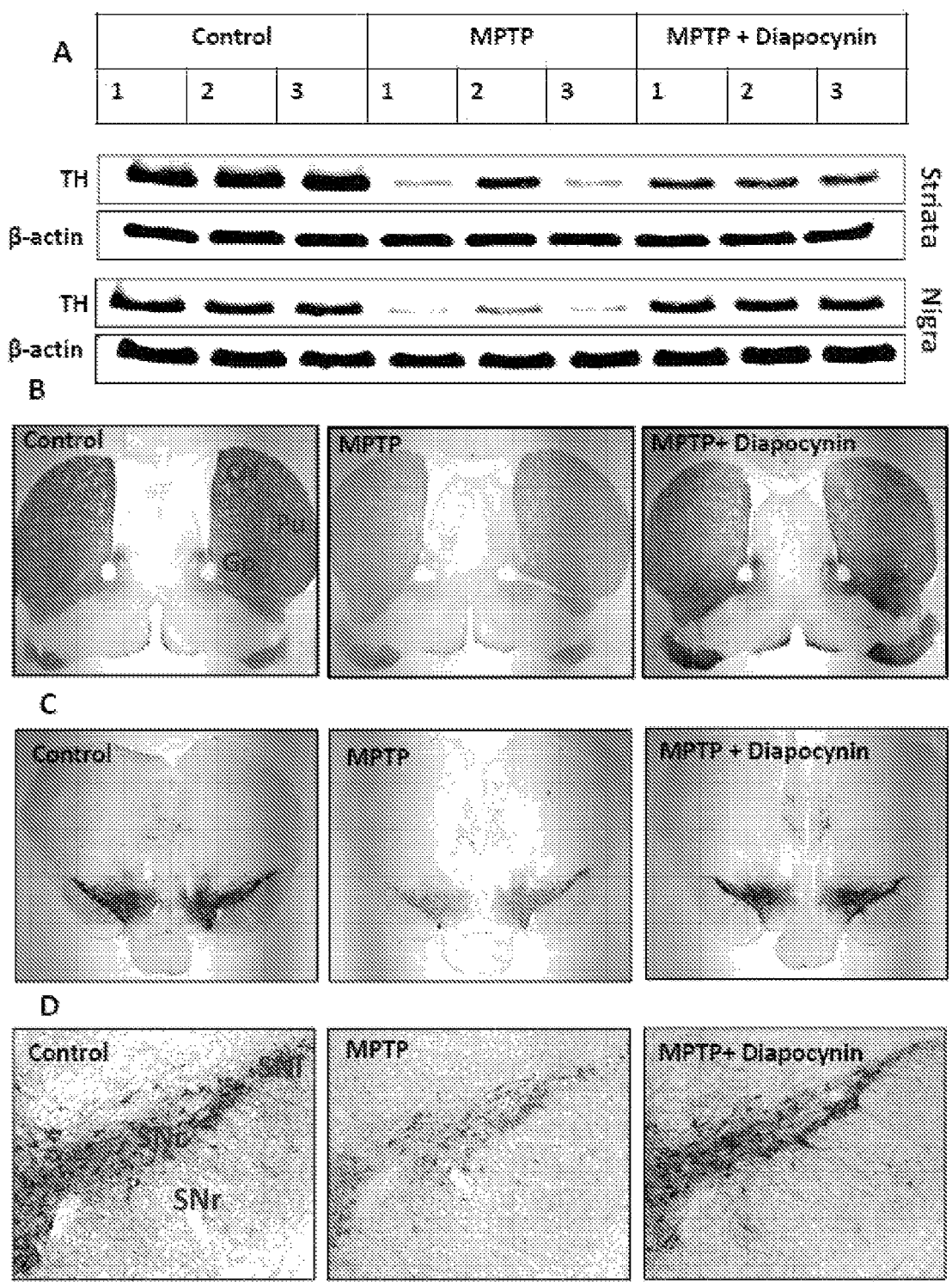
FIG. 13 shows the neuroprotective effect of Diapocynin against MPTP-induced loss of nigrostriatal dopaminergic neurons. Striatal and substantia nigra tissues were processed for Western blot analysis to check the expression levels of tyrosine hydroxylase (TH) in striatum and substantia nigra (panel A). Tyrosine hydroxylase—DAB immunostaining was performed in striatum (panel B, magnification is ×2) and substantia nigra (panel C, 2× magnification and panel D, 10× magnification). CN: Caudate nucleus, Pu: Putamen, GP: Globus pallidus, SNc: Substantia nigra compacta, SNr: Substantia nigra reticularis, and SNl: Substantia nigra lateralis.

As diapocynin significantly prevents loss of the dopamine, DOPAC, and HVA levels due to MPTP toxicity, we examined whether diapocynin could protect the nigrostriatal axis against MPTP toxicity. Reduced levels of TH expression in MPTP-treated mice both in striatum and substantia nigra were observed by Western blot and immunohistochemical analyses (FIG. 13, panels A-D). However, MPTP- and diapocynin-treated mice showed less reduction of expression of TH (FIG. 13, panel A). TH-DAB immunostaining revealed the loss of dopaminergic neuron terminals in putamen, caudate nucleus and globus pallidus regions of striatum (FIG. 13, panel B) and loss of dopaminergic cell bodies in par-compacta and lateralis regions of substantia nigra of MPTP-treated mice (FIG. 13, panels C and D). However, with diapocynin treatment, the loss of TH-positive neurons and terminals is substantially prevented in both the striatum and substantia nigra (FIG. 13, panels C and D). Therefore, treatment with diapocynin appears to have substantial potential neuroprotective effects in the nigrostriatal axis.

Assessment of Neuroprotective Effect of Diapocynin in MPTP-Induced Animal Model of PD by FLUORO-JADE B® Staining.

Figure 14:
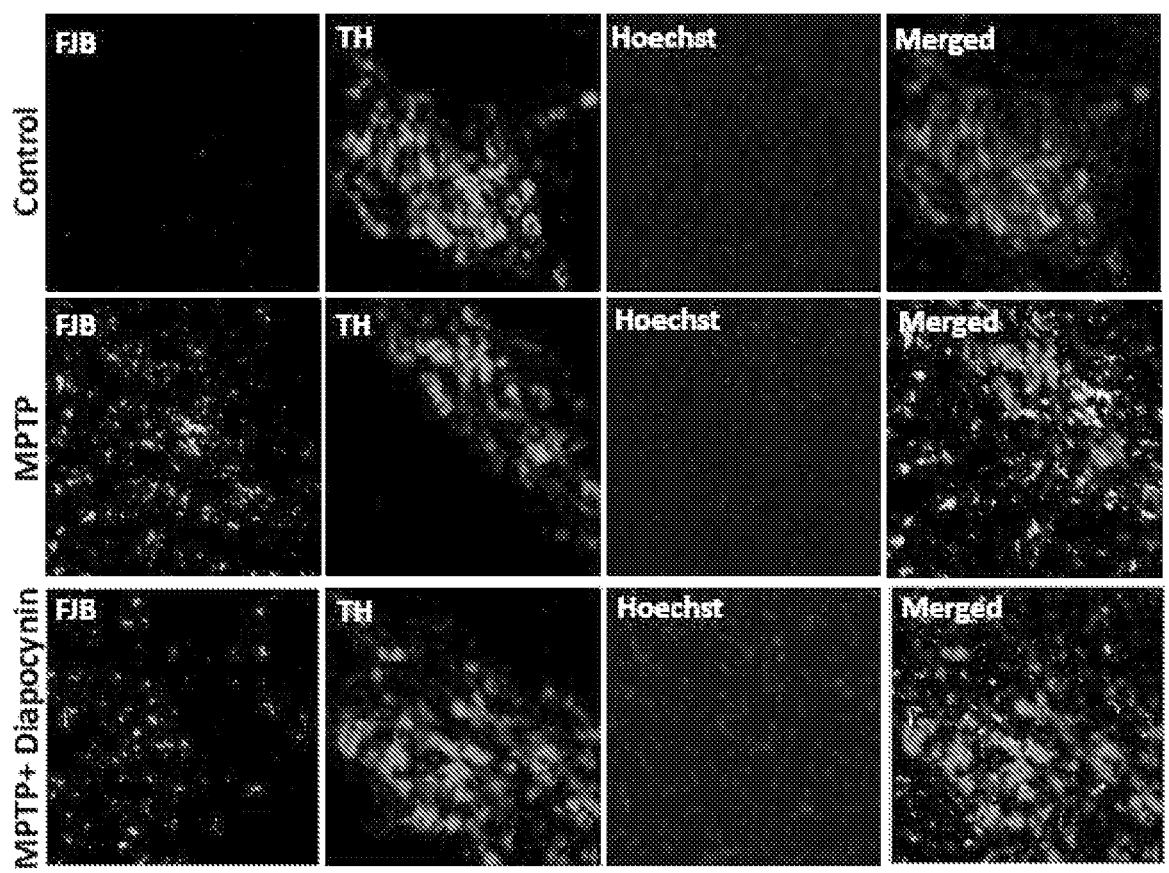
FIG. 14 shows that diapocynin protects neuronal degeneration in MPTP model of PD as measured by tyrosine hydroxylase (TH) and FLUORO-JADE B® (FJB) double-labeling. Substantia nigra sections were processed for tyrosine hydroxylase (TH) and FJB double-label staining. Nuclei were stained with Hoechst 33442.

To further confirm that diapocynin protects against MPTP-induced dopaminergic neurodegeneration, we performed double-labeling of TH and FLUORO-JADE B® in mice substantia nigra sections. FLUORO-JADE B® effectively stains degenerating neurons and is also a marker of neuronal damage (67). Apoptotic as well as necrotic cell deaths have been suggested in PD (47 and 68). As anticipated, a decreased number of TH-positive neurons was detected in MPTP-treated sections, which correlated with an increased number of FLUORO-JADE B®-stained cells, indicating neurodegeneration of the substantia nigra in MPTP-treated mice (FIG. 14). Interestingly, MPTP- and diapocynin-treated mice showed fewer FLUORO-JADE B®-positive cells, indicating attenuation of neurodegeneration by diapocynin. As expected, increases in TH-positive cells were also observed with MPTP- and diapocynin-treated mice. Collectively, these data indicate that diapocynin protects against MPTP-induced death of dopaminergic neurons in substantia nigra. These data further underline the potential neuroprotective effects of diapocynin against PD-associated dopaminergic neurodegeneration.

Example 4

Evaluation of Anti-Neuroinflammatory Effect of Diapocynin in Microglial Cell Culture Models of Neuroinflammation Chemicals and Biological Reagents.

RPMI, Trypsin-EDTA, DMEM-F12, FBS, sodium pyruvate, penicillin/streptomycin, NEAA, and glutamine (Q) were all obtained from Invitrogen. Griess Reagent was purchased from Sigma-Aldrich (St. Louis, Mo.). A Bradford protein assay kit was purchased from Bio-Rad Laboratories (Hercules, Calif.). Protease and phosphatase inhibitors were obtained from Pierce Biotechnology (Rockford, Ill.). All primary antibodies were purchased from Santa Cruz Biotechnology, Inc. Li-Cor blocking buffer was obtained from LI-COR Biosciences. Alexa Fluor 680 (donkey anti-mouse) was used as a secondary antibody and obtained from Invitrogen. IRDye800 Conjugated Anti-Rabbit IgG was obtained from Rockland Immunochemicals (Gilbertsville, Pa.). Luminex block/store buffer reagents (Sigma P-3688 and sodium azide) were purchased from Sigma-Aldrich (St. Louis, Mo.). Streptavadin-PE, capture antibodies, and detection antibodies were purchased from eBioscience (San Diego, Calif.). The 96-well filter plates were purchased from Fisher Scientific (Pittsburgh, Pa.).

Cell Culture Models of Neuroinflammation.

Two cell models of neuroinflammation were used to evaluate the anti-neuroinflammatory property of diapocynin including the mouse BV2 microglial cell line, as well as primary microglia isolated from mouse brains. BV2 cells were obtained from the American Tissue Culture Collection. BV2 cells were maintained in RPMI containing 10% FBS and 100 units of pen/strep at 37° C. and 5% $CO_2$. For treatments, RPMI containing 2% FBS and 100 units of pen/strep was used.

Primary Microglia.

Primary microglia were obtained from 1-2 day old C57/b16 mouse pups. Upon collection, whole brains were kept in ice-cold DMEM-F12 medium containing 10% FBS, 1× sodium pyruvate, 1× NEAAs, 100 units pen/strep, and Q. After collection, the brains were placed in 0.25% trypsin-EDTA and incubated at 37° C., with gentle shaking every 5-10 min. After 30 min, the trypsin was removed, and the brains are washed in warmed medium twice. After washing, medium was added to the brains, and the brains were homogenized using gentle pipetting, starting with a 25 ml pipette and moving to smaller pipette tips as the brains were broken up. When the brains were sufficiently homogenized to a single-cell suspension, they were filtered with a 70 μm nylon filter, which allowed microglia and astrocytes to be collected. The resultant cell suspension was plated in T-75 flasks and allowed to grow for 12-14 days at 37° C., 5% $CO_2$. Microglia were collected using an Easy Sep Magnet (Stemcell Technologies, Vancouver, BC, Canada) (68-69) and plated on poly-D-lysine-coated plates and allowed to attach for 2-4 days before treatment.

iNOS or NOS-2 Activation Assessment.

Inducible nitric oxide synthase (iNOS or NOS2) activation was assessed by measuring nitrite levels using Griess reagent in a 96-well format (70-72). Each well contained 40,000 BV2 cells or 100,000 primary microglia. BV2 cells were cultured in 150 μl of RPMI containing 10% FBS and pen/strep, and the primary microglia were cultured in DMEM-F12 containing 10% FBS, pen/strep, sodium pyruvate (S/P), Q, and NEAAs. One day after culturing, cells were replaced with 150 μl of their respective complete media containing only 2% FBS. Both cell types were pretreated with diapocynin (10 μM) and apocynin (100 μM) for 30 min before LPS stimulation (1 μg/ml LPS for BV2 cells and 100 ng/ml for primary microglia), and the plates were incubated at 37° C. After 24 hr at 37° C., 100 μl of supernatant were removed and placed into a new 96 well plate, to which 100 μl of Griess reagent were added. The plate was shaken on a plate shaker for 10 min before being read in a plate reader at 540 nm.

Measurements of Cytokines by LUMINEX® Immunoassay.

Cytokine levels of BV2 and microglial cells treated with diapocynin were determined by LUMINEX® multiplex immunoassay. Each well containing 40,000 BV2 cells in 150 μl of RPMI, 10% FBS and Pen/strep or 100,000 primary microglia in DMEM-F12 containing 10% FBS, Pen/strep, S/P, Q, and NEAAs were prepared. During treatment, cells received 150 μl of their respective complete media with only 2% FBS. Both diapocynin (10 μM) and apocynin (100 μM) were added 30 min before treatment LPS treatment (1 μg/ml LPS for BV2 cells, 500 ng/ml LPS for primary microglia), but remained in the supernatant for the entire 24 hr treatment period at 37° C. After 24 hr, supernatant was collected and frozen at −20° C. for subsequent analysis. For analysis, the supernatant was thawed and 40 μl of each supernatant sample was tested using the LUMINEX® protocol according to the manufacturer's instructions (73-74).

Cytokine standards and controls were adjusted to 40 μl volume and the LUMINEX® Samples were run on a LUMINEX® 200 Total System and analyzed with Multiplex Analysis—LUMINEX® Software (Invitrogen, Carlsbad, Calif.).

Western Blot.

BV2 cell lysates containing equal amounts of protein were loaded in each lane and separated on a 10% SDS-PAGE gel. After separation, the protein was transferred to a nitrocellulose membrane. Non-specific binding sites were blocked with Li-cor blocking buffer for 45 min. The membranes were then treated with primary antibodies directed against NOS2 (mouse monoclonal 1:200) and p67phox (rabbit polyclonal 1:200). To confirm equal amounts of protein were loaded, membranes were also probed for β-actin with a β-actin antibody (dilution of 1:10,000). Secondary antibodies, donkey anti-mouse (Invitrogen) and conjugated anti-rabbit IgG (Rockland), were used at a dilution of 1:10,000 for 1 hr at room temperature. The membranes were imaged and captured using a Li-COR Odyssey infrared imaging system and software.

Data Analysis.

Data analysis was performed using Prism 4.0 software (GraphPad Software, Inc.). Raw data were first analyzed using one-way ANOVA, and then Tukey's post-test was used to compare all treatment groups. Differences with $P<0.05$ were considered significant.

Example 4

Results

Diapocynin is More Effective than Apocynin at Attenuating LPS-Induced iNOS Activation in Both BV2 Microglia Cells and Primary Microglia.

Figure 15A:
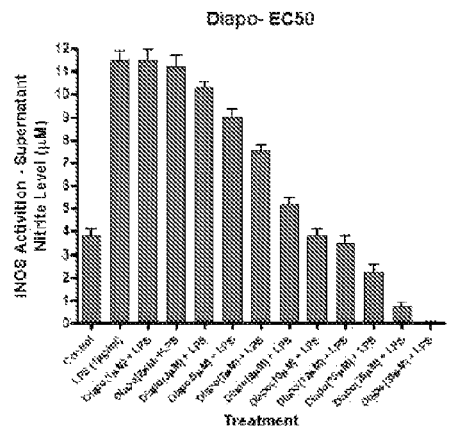
FIG. 15A shows the ability of diapocynin to attenuate LPS-induced nitrative stress in the BV2 microglial cell model. BV-2 cells were treated with different concentrations of diapocynin and incubated for 30 min before the addition of 1 µg/ml of LPS. The cells were then assessed for nitrite level using Griess reagent. Values are mean±SEM (n=6)
Figure 15B:
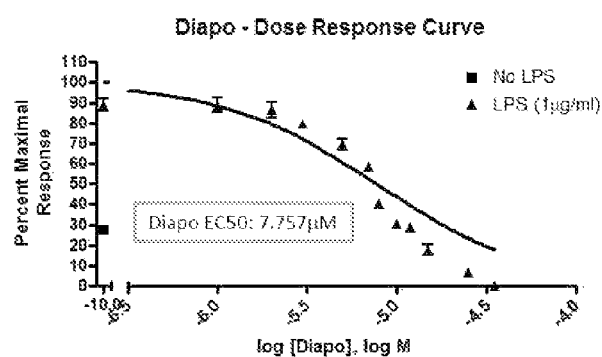
FIG. 15B shows a diapocynin (Diapo) dose response curve of the data represented in FIG. 15A that indicates the EC50 of diapocynin. The data were transformed according to log dose, normalized according to the highest and lowest concentrations, and then graphed based on a non-linear regression curve.
Figure 16A:
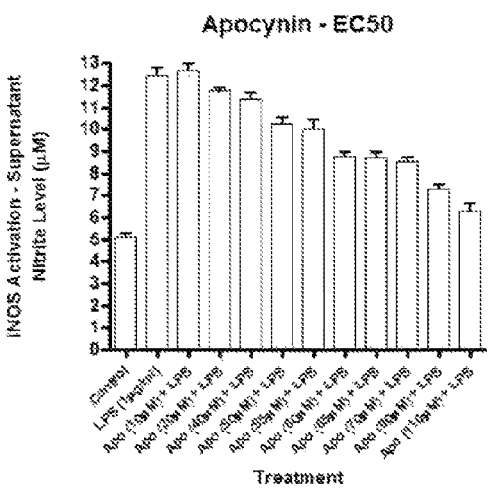
FIG. 16A shows the ability of apocynin to attenuate LPS-induced nitrative stress in the BV2 microglial cell model. BV-2 cells were treated with different concentrations of apocynin and incubated for 30 min before the addition of 1 µg/ml of LPS. The cells were then assessed for nitrite level using Griess reagent. Values are mean±SEM (n=6)
Figure 16B:
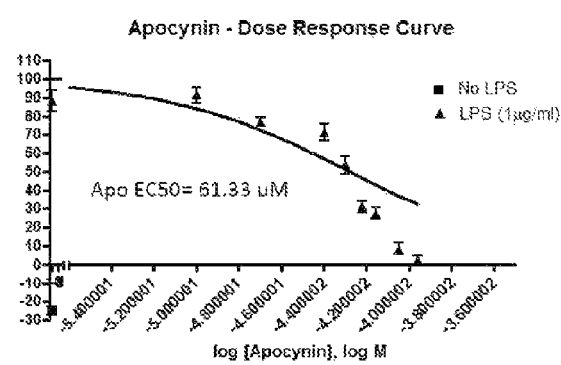
FIG. 16B shows an apocynin dose response curve of the data represented in FIG. 16A that indicates the EC50 of diapocynin. The data were transformed according to log dose, normalized according to the highest and lowest concentrations, and then graphed based on a non-linear regression curve. The EC50 was calculated using GRAPHPAD PRISM® software.
Figure 17:
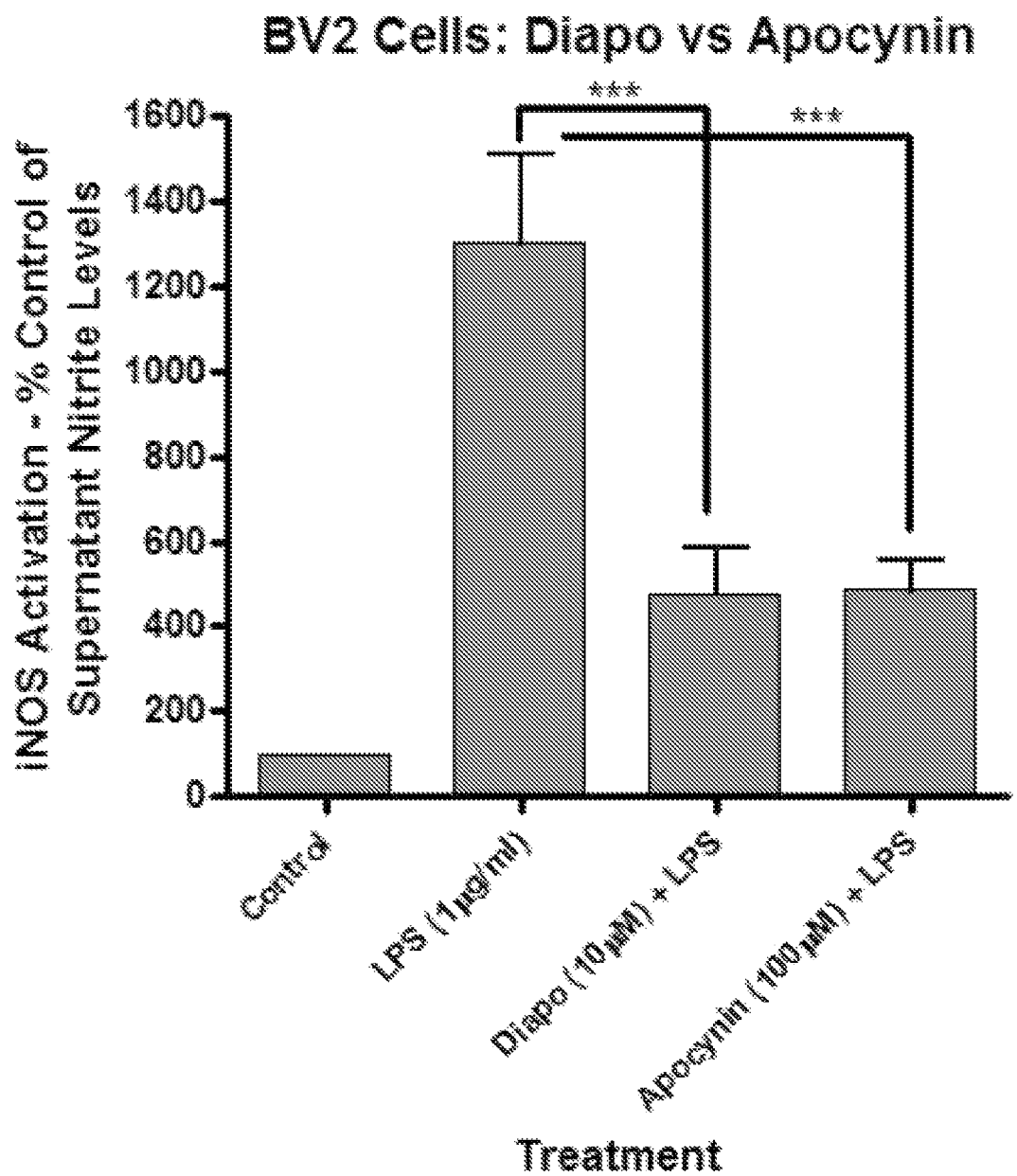
FIG. 17 shows a comparison of diapocynin and apocynin on LPS-induced nitrative stress in BV2 microglial cell model. BV-2 cells were pretreated with diapocynin (10 µM) and apocynin (100 µM) for 30 min and then stimulated with LPS (1 µg/ml) for 24 hr prior to measuring nitrite levels by the Griess method. Values are mean percent control±SEM (n=6)
Figure 18:
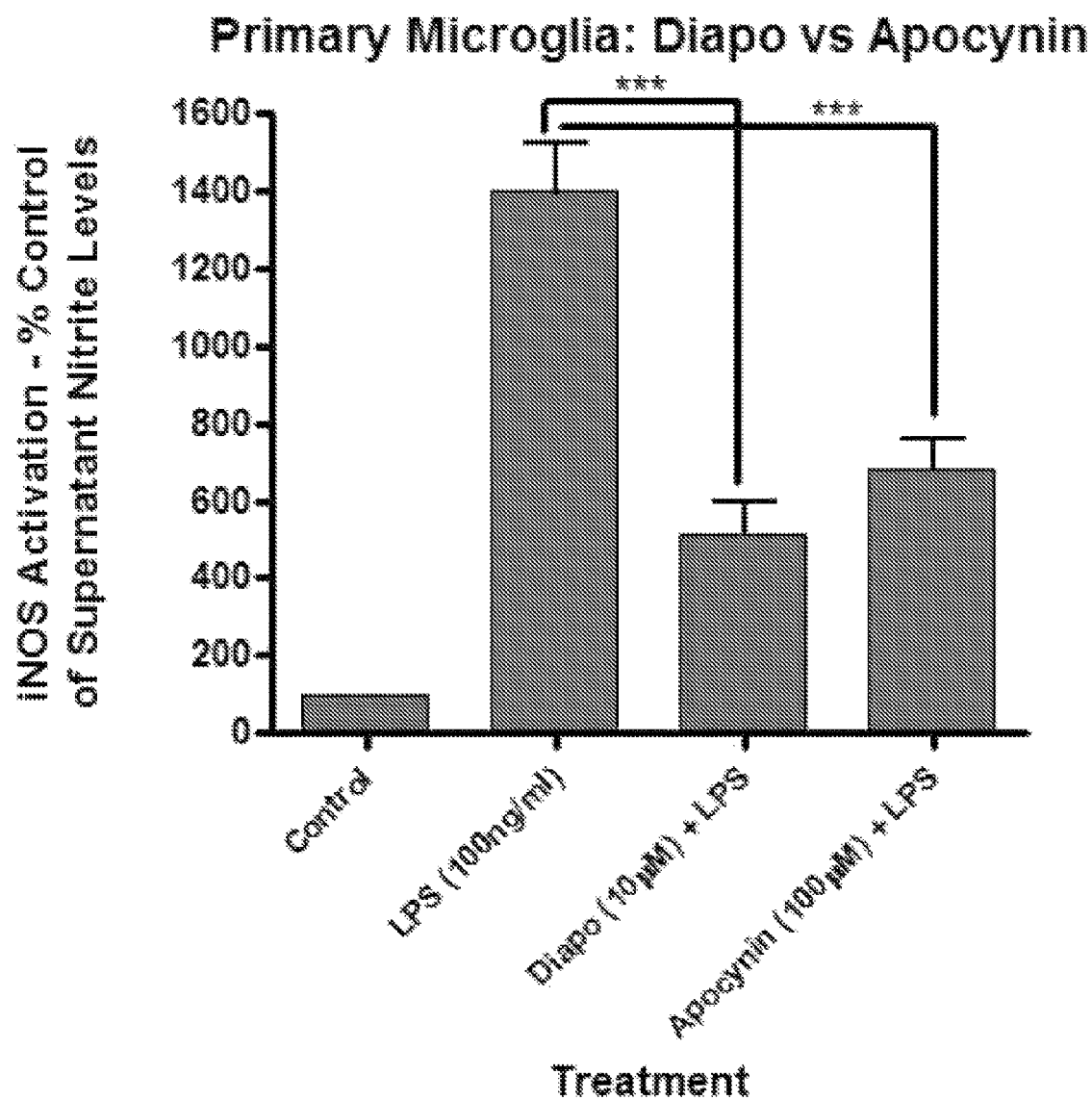
FIG. 18 shows a comparison of diapocynin (diapo) and apocynin on LPS-induced nitrative stress in mouse primary microglia. Mouse primary microglia were pretreated with diapo (10 µM) and apocynin (100 µM) for 30 min and then stimulated with LPS (1 µg/ml) for 24 hr prior to measuring nitrite levels by Griess method. Values are expressed as mean percent control±SEM (n=7)

First, we examined what concentrations of diapocynin (FIGS. 15A and 15B) and apocynin (FIGS. 16A and 16B) are necessary to block LPS-induced iNOS activation by creating a dose response curve. From the dose response curves, the EC50 of each compound was deciphered. The EC50 of diapocynin is 7.757 μM, whereas apocynin's EC50 is 61.33 μM. Based on EC50 values, diapocynin was used in further experiments at a concentration of 10 μM, while apocynin was used at a concentration of 100 μM. We showed that diapocynin, even at a 10× lower concentration, is just as effective at attenuating LPS-induced iNOS activation as apocynin in both BV2 cells (FIG. 17) and primary microglia (FIG. 18).

Effect of Diapocynin on LPS-Induced Cytokine Release in Primary Microglia.

Figure 19A:
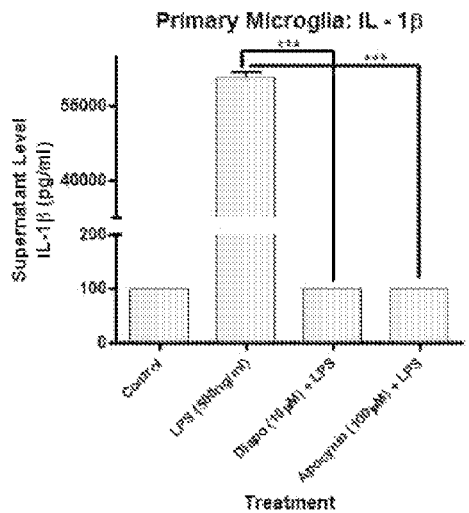
FIG. 19A shows diapocynin (diapo) suppresses LPS-induced IL-1β release in primary mouse microglia. Mouse primary microglia was pretreated with diapo (10 µM) and apocynin (100 µM) for 30 min and then stimulated with LPS (1 µg/ml for 24 hr) prior to measuring IL-1β levels. Values are expressed as mean pg/ml±SEM (n=4)
Figure 19B:
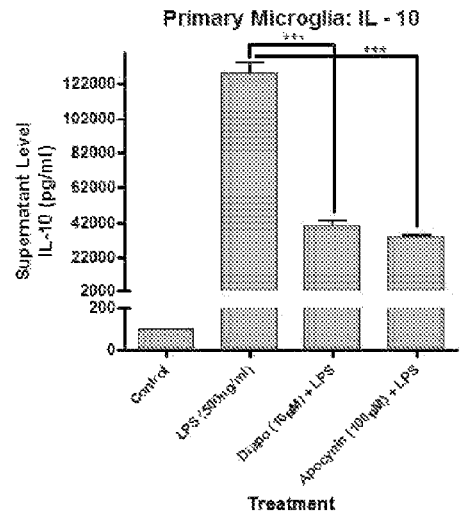
FIG. 19B shows diapocynin (diapo) suppresses LPS-induced IL-10 release in primary mouse microglia. Mouse primary microglia was pretreated with diapo (10 µM) and apocynin (100 µM) for 30 min and then stimulated with LPS (1 µg/ml) for 24 hr prior to measuring IL-10 levels. Values are expressed as mean pg/ml±SEM (n=4)
Figure 19C:
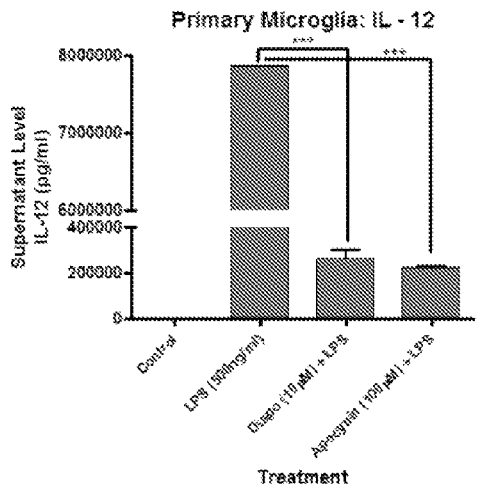
FIG. 19C shows diapocynin (diapo) suppresses LPS-induced IL-12 release in primary mouse microglia. Mouse primary microglia was pretreated with diapo (10 µM) and apocynin (100 µM) for 30 min and then stimulated with LPS (1 µg/ml) for 24 hr prior to measuring IL-12 levels. Values are expressed as mean pg/ml±SEM (n=4)
Figure 19D:
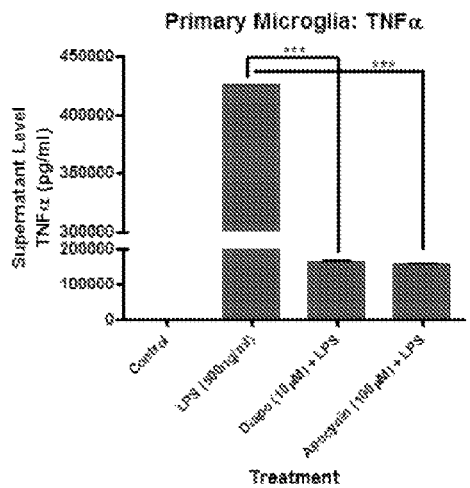
FIG. 19D shows diapocynin (diapo) suppresses LPS-induced TNF-α release in primary mouse microglia. Mouse primary microglia was pretreated with diapo (10 µM) and apocynin (100 µM) for 30 min and then stimulated with LPS (1 µg/ml) for 24 hr prior to measuring TNF-α levels. Values are expressed as mean pg/ml±SEM (n=4)

Since diapocynin was able to attenuate LPS-induced iNOS activation, we next examined its ability to block known inflammatory cytokine release from microglia. We compared the 10 fold lower diapocynin (10 μM) compared to apocynin (100 μM). Measurement of cytokine release in supernatant was determined by the LUMINEX® assay. We found that diapocynin was very effective in blocking LPS-induced release of IL-1β (FIG. 19A), IL-10 (FIG. 19B), IL-12 (FIG. 19C), and TNF-α (FIG. 19D). Apocynin was also effective but required 10× higher concentration than diapocynin. Collectively, these results demonstrate that diapocynin is more potent than apocynin in blocking primary microglia-mediated neuroinflammatory response.

Diapocynin has the Ability to Attenuate LPS-Induced Increases in iNOS and p67phox Protein Expression.

Figure 20:
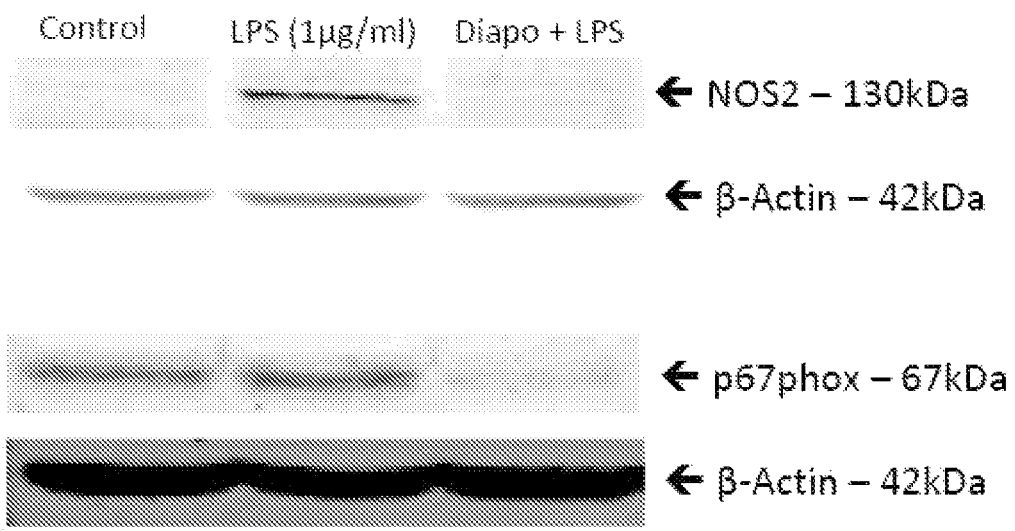
FIG. 20 illustrates that diapocynin (diapo) suppresses LPS-induced NOS-2 and p67phox expression in BV2 microglial cells. BV2 microglial cells were pretreated with diapo (10 µM) for 30 min and then stimulated with LPS (1 µg/ml) for 24 hr prior to measuring NOS-2 and p67phox expression by Western blot. β-actin was used as loading control.

After demonstrating that diapocynin has the ability to block the release of key inflammatory molecules, we examined diapocynin's ability to block the expression of key inflammatory proteins. We chose to examine NOS2 and p67phox expression within BV2 cells. NOS2 is the inducible nitric oxide synthase protein that is responsible for much of the release of nitrite from the cells upon LPS stimulation. The p67phox protein is one of the key activating subunits in the NADPH oxidase complex 2 (NOX2), which is responsible for production and release of reactive oxygen species (ROS) from activated microglia. As shown in FIG. 20, diapocynin was extremely effective in reducing LPS-induced NOS2 and p67phox protein expression back to basal level or even below the basal level. Taken together, these results demonstrate that diapocynin has anti-inflammatory effects by attenuating microglial-mediated inflammatory responses such as cytokine release, NOS2 and NOX2 activation.

Example 5

Evaluation of Anti-Neuroinflammatory Effect of Diapocynin Diacetate in a Microglial Cell Culture Model of Neuroinflammation This example generally followed the cell culture, treatment, and analysis steps of Example 4 above.

Figure 21:
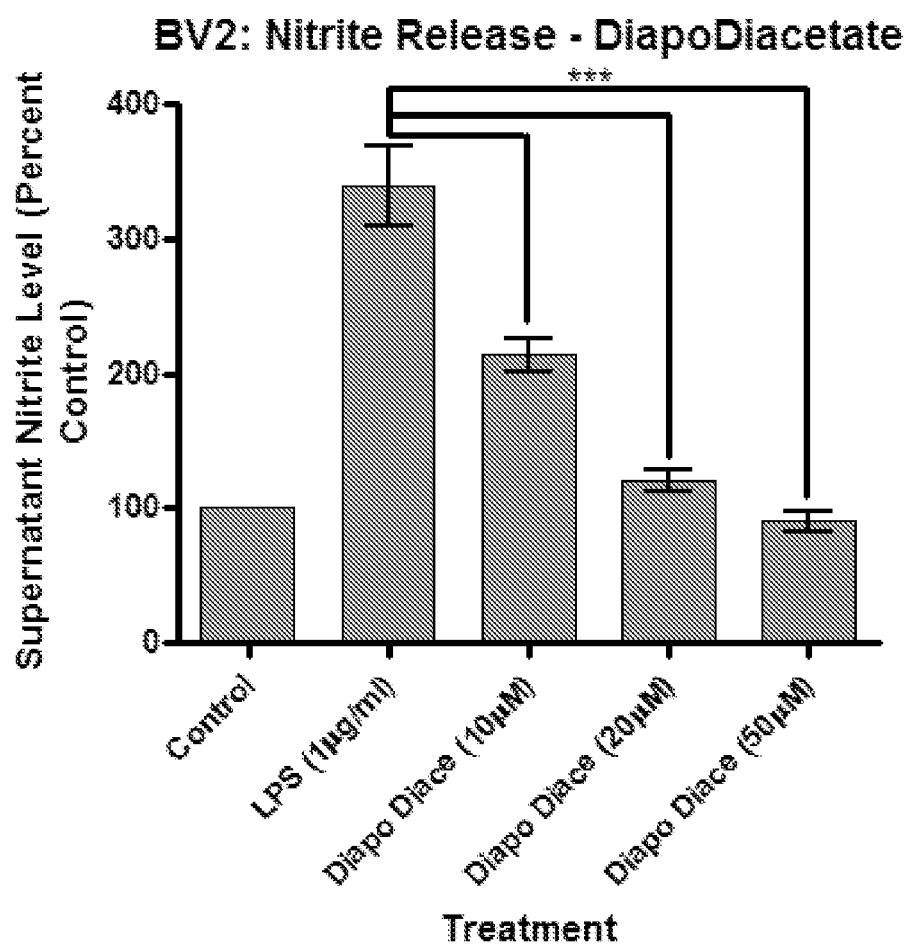
FIG. 21 illustrates that diapocynin (diapo) diacetate (diapo diace) suppresses LPS-induced NOS-2 in BV2 microglial cells. Diapo diacetate was used on the cells as a 30 min pretreatment, then LPS (1 µg/ml) was added. All treatments were allowed to incubate at 37° C. for 24 hr, starting from the addition of LPS. The percent nitrite level for the treatments was compared to control.

Diapocynin diacetate (diapodiacetate or diapo diace) suppresses LPS-induced NOS-2 in BV2 microglial cells (FIG. 21). BV-2 cells were plated in 96 well plates, 40,000 cells per well, and treated in 150 μl of RPMI containing 2% heat inactivated FBS and penicillin/streptomycin. Diapo diacetate was used on the cells as a 30 min pretreatment, then LPS (1 μg/ml) was added. All treatments were allowed to incubate at 37° C. for 24 hr, starting from the addition of LPS. One hundred microliter aliquots of supernatant from each well were combined with 100 μl of Griess reagent (Sigma) in a 96-well plate and allowed to shake for 10 minutes before being read on the plate reader. The percent nitrite level for the treatments compared to the control was graphed.

While the present invention has been described and exemplified with some specificity, those skilled in the art will appreciate the various modifications, including variations, additions, and omissions that may be made in what has been described. It is intended that these modifications may also be encompassed by the present invention and that the scope of the present invention be limited solely by the broadest interpretation that lawfully can be accorded the appended claims. All references and publications listed herein are incorporated by reference.

RELATED PUBLICATIONS

1. Parker W D Jr et al. *Ann Neurol* 26:719-723, 1989;
2. Klees R F et al. Apocynin derivatives interrupt intercellular signaling resulting in decreased migration in breast cancer cells. *J Biomed Biotechnol:* 1-10, 2006;
3. Steffen Y. Mono-O-methylated flavanols and other flavonoids as inhibitors of endothelial NADPH oxidase. *Arch Biochem Biophys* 469:209-219, 2008;
4. Heumuller S et al. Apocynin is not an inhibitor of vascular NADPH oxidases but an antioxidant. *Hypertension* 51:211-217, 2008;
5. Harraz M M. et al. SOD1 mutations disrupt redox-sensitive Rac regulation of NADPH oxidase in a familial ALS model. *J Clin Invest* 118:659-670, 2008;
6. Lin M T et al. *Nature* 443:787-802, 2006;
7. Schapira A H V. *Lancet* 368:70-82, 2006;
8. Schon E A et al. *J Clin Invest* 111:303-312, 2003;
9. Beal M F. *Curr Opin Neurobiol* 6:661-666, 1996;
10. Greenamyre J T et al. *Trends Neurosci* 24:247, 2001;
11. Betarbet R et al. Chronic systemic pesticide exposure reproduces features of Parkinson's disease. *Nat Neurosci* 3(12):1301-1306, 2000;
12. Götz M E et al. Oxidative stress: free radical production in neural degeneration. *Pharmacol Ther* 63:37-122, 1994;
13. Qian Z M et al. Expression of iron transport proteins and excessive iron accumulation in the brain in neurodegenerative disorders. *Brain Res Rev* 27:257-267, 1998;
14. Good P F et al. Protein nitration in Parkinson's disease. *J Neuropathol Exp Neurol* 57:338-342, 1998;

15. Kieburtz K. Issues in neuroprotection clinical trials in Parkinson's disease. *Neurology* 66, (10 Suppl 4):S50-57, 2006;
16. Kaur D et al. Genetic or pharmacological iron chelation prevents MPTP-induced neurotoxicity in vivo: a novel therapy for Parkinson's disease. *Neuron* 37:899-909, 2003;
17. Stefanska J, Pawliczak R. Apocynin: molecular aptitudes. Mediators Inflamm. 2008; 2008: 106507. Epub 2008 Dec. 2;
18. Hirsch, E C, Hunot S (2009) Neuroinflammation in Parkinson's disease: a target for neuroprotection? Lancet Neurol 8:382-397;
19. O'Callaghan J P, et al. (2008) Defining "Neuroinflammation" Lessons from MPTP- and methamphetamine-induced neurotoxicity. Ann. New York Academy Sciences 1139; 318-330;
20. Von Bernhardi R et al. (2010) Aging-dependent changes of microglial cells and their relevance for neurodegenerative disorders. J Neurochemistry 112; 1099-1114;
21. McNaull, B B A et al. (2010) Inflammation and anti-inflammatory strategies for Alzheimer's disease-A mini-review. Gerontology 56; 3-14;
22. Lee Mosley R, Gendelman (2010) Control of neuroinflammation as a therapeutic strategy for amyotrophic lateral sclerosis. Experimental Neurology 222:1-5;
23. Tansey M G, et al. (2008) Neuroinflammatory mechanisms in Parkinson's disease: Potential environmental triggers, pathways, and targets for early therapeutic intervention. Experimental Neurology 208; 1-25;
24. Smith R A J et al., 1999, *Eur J Biochem* 263:709-716;
25. Smith R A J et al., 2003, *Proc Natl Acad Sci USA* 100: 5407-5412;
26. Murphy M P, 1997, *Trends Biotechnol* 15:326-330;
27. Smith R A et al., 2004, *Methods Enzymol* 382:45-67;
28. Cafiso D S, 1989, *Methods Enzymol* 172:331-345;
29. Dhanasekaran A et al., 2005, *Free Rad Biol Med* 39:567-583;
30. Jackson-Lewis V et al., 2007, *Nat Protocols* 2:141-151;
31. Mizuno Y et al., 1988, *Neurosci Lett* 91:349-353;
32. Langston J W et al., 1983, *Science* 219:979-980;
33. Davis G C et al., 1979, *Psychiatry Res* 1:249-254;
34. Burns R S et al., 1984, *Proc Natl Acad Sci USA* 80:4546-4550;
35. Przedborksi S et al., 1998, *Mov Disord* 13(Suppl 1):35-38;
36. Langston J W et al., 1984, *Science* 225:1480-1482;
37. Forno L S et al., 1993, *Adv Neurol* 60:600-608;
38. Langston J W et al., 1984, *Brain Res* 292:390-394;
39. Heikkila R E et al., 1984, *Nature* 311:467-469;
40. Sherer T B et al., 2002, *Neuroscientist* 8:192-197;
41. Ramsay R R et al., 1987, *Arch Biochem Biophys* 259:645-649;
42. Hasegawa E et al., 1990, *Biochem Biophys Res Commun* 170:1049-1055;
43. Schapira A H et al. *J Neurochem* 54:823-827;
44. Schapira A H V, 2006, *Lancet* 368:70-82;
45. Jha N et al., 2000, *J Biol Chem* 275:26096-101;
46. Krüger R et al., 2000, *J Neural Transm* 107:31-40;
47. Turmel H et al., 2001, *Mov Disord* 16:185-189;
48. Zhang D et al., 2007, *J Pharmacol Exp Ther* 322:913-922;
49. Jackson-Lewis V, Przdborski S. (2007) Protocol for the MPTP mouse model of Parkinson's disease. Nature Protocols 2; 141-151;
50. Berge S M et al., "Pharmaceutical Salts." *J. Pharm. Sci.* 66:1-19 (1977);
51. Haynes D A et al., "Occurrence of pharmaceutically acceptable anions and cations in the Cambridge Structural Database," *J. Pharm. Sci.* 94:2111-2120 (2005);
52. Thomas G, Medicinal Chemistry: An Introduction, 2000, John Wiley & Sons, Ltd. pp. 12, 17, 243 and 364-372);
53. Wermuth C G, 2003, The Practice of Medicinal Chemistry, 2nd Ed., Academic Press 33:561-582;
54. Hanson J R, 1999, *Protecting Groups in Organic Synthesis*, Sheffield Academic Press, 2:8-35
55. Kim H J et al., 2007, *Brain Res* 1181:130-41;
56. Ghosh et al., 2009, J Neurosci 29:1343-13556;
57. Ghosh et al, 2007, Proc Natl Acad Sci USA 104:18754-18759;
58. Bian et al., 2007, Brain Res 1150:55-61;
59. Wu et al., 2002, J Neurosci 22:1763-1771;
60. Dauer and Prezedborski, 2003, Neuron 39: 889-909;
61. Wu and Przedborski et al., 2003, J Neurosci 22:1763-1771;
62. Stadler et al., 2008, Free Radic Biol Med 45: 866-874;
63. Awasth et al., 2008, Free Radic Biol Med 45: 111-118;
64. Selley et al., 1998, Free Radic Biol Med 25: 169-174;
65. Hunot et al., 1976, Proc Natl Acad Sci USA 94:7531-7536;
66. Benner et al, 2004, Proc Natl Acad Sci USA 101:9435-9440;
67. Kanthasamy et al., 1999, *J. Pharmacol. Exp. Ther.,* 288: 1340-1348;
68. Kortylewski M, Kujawski M, Herrman A, Yang C, Wang L, Liu Y, Salcedo R, and Yu H. Toll-like Receptor 9 Activation of Signal Transducer and Activator of Transcription 3 Constrains Its Agonist-based Immunotherapy. *Cancer Research,* 69(6): 2497-2505, 2009;
69. Kortylewski M, Xin H, Kujawski M, Lee H, Liu Y, Harris T, Drake C, Pardon D and Yu H. Regulation of the IL-23 and IL-12 Balance by Stat3 Signaling in the Tumor Microenvironment. *Cancer Cell,* 15(2): 114-23, 2009;
70. Chae, S. Y. et al. Protection of insulin secreting cells from nitric oxide induced cellular damage by crosslinked hemoglobin. *Biomaterials* 25, 843-50, 2004;
71. Campos-Neto, A., et al. CD40 ligand is not essential for the development of cell mediated immunity and resistance to *Mycobacterium tuberculosis. J. Immunol.* 160, 2037-2041, 1998;
72. Kleinbongard P et al. Griess method for nitrite measurement of aqueous and protein-containing samples. Methods Enzymol. 2002; 359:158-68;
73. E. Gorelik, D. P. Landsittel, A. M. Marrangoni, F. Modugno, L. Velikokhatnaya and M. T. Winans et al. Multiplexed immunobead-based cytokine profiling for early detection of ovarian cancer. *Cancer Epidemiol Biomarkers Prev,* 14(4): 981-7, 2005; and
74. de Jager, W., et al. Simultaneous detection of 15 human cytokines in a single sample of stimulated peripheral blood mononuclear cells. *Clin Diagn Lab Immunol,* January, 10(1): 133-9, 2003.

We claim:

1. An apocynin derivative or apocyanin derivative dimer selected from the group consisting of:

(a):

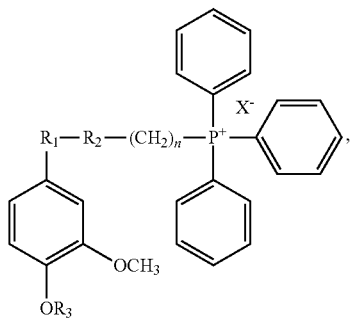

wherein $R_1$ is C=O, (CH=CH) or $CH_2$,
wherein $R_2$ is O, NH or COO,
wherein $R_3$ is H, $COCH_3$ or $CO(CH_2)_m CH_3$,
wherein $X^-$ is $Cl^-$, $Br^-$, or $I^-$,
wherein n is 2-16, and
wherein m is 1-16;

(b):

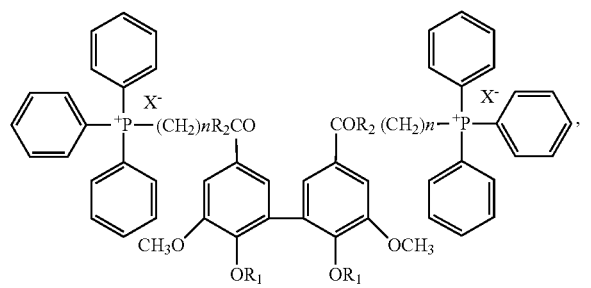

wherein $R_1$ is H, $COCH_3$, or $CO(CH_2)_m CH_3$,
wherein $R_2$ is O or NH,
wherein $X^-$ is $Cl^-$, $Br^-$, or $I^-$,
wherein n is 2-16, and
wherein m is 1-16;
and a prodrug, solvate or hydrate of any of structures (a)-(b).

2. A pharmaceutical dosage form comprising the apocynin derivative or apocyanin derivative dimer of claim 1 and a pharmaceutically suitable carrier system.

3. The pharmaceutical dosage form of claim 2, wherein the dosage form comprises an oral, injection, infusion, inhalation, transdermal, or implant dosage form.

4. A method of administering a therapeutically effective amount of an apocynin derivative or apocyanin derivative dimer of claim 1 to a mammal, to obtain an increase in the amount of dopamine in the brain of the mammal or an increase in the amount of dihydroxyphenylacetic acid (DOPAC) in the mitochondria of the mammalian brain cell.

5. The method of claim 4, wherein the apocynin derivative or apocyanin derivative dimer is orally administered.

6. The apocynin derivative according to claim 1, wherein the apocynin derivative has any one of the following structures:

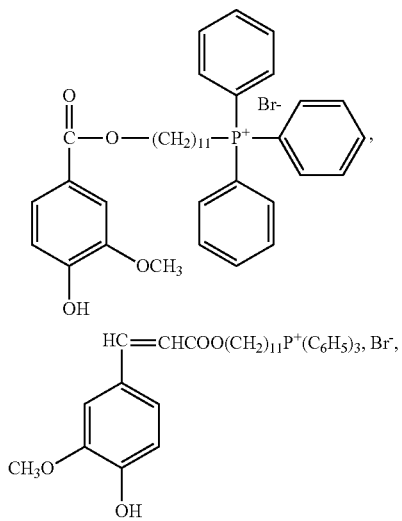

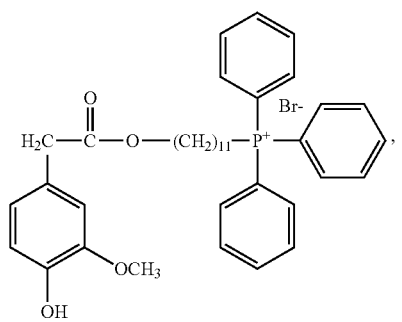

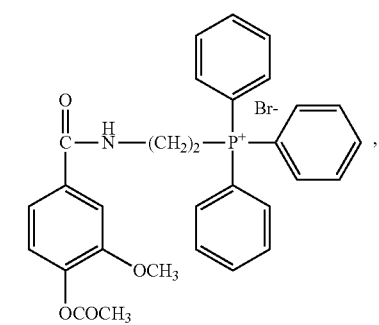

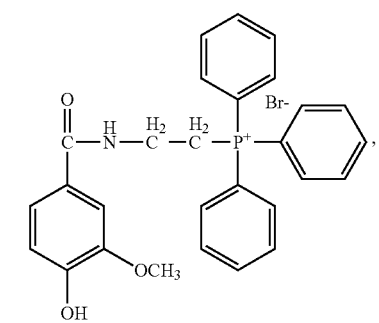

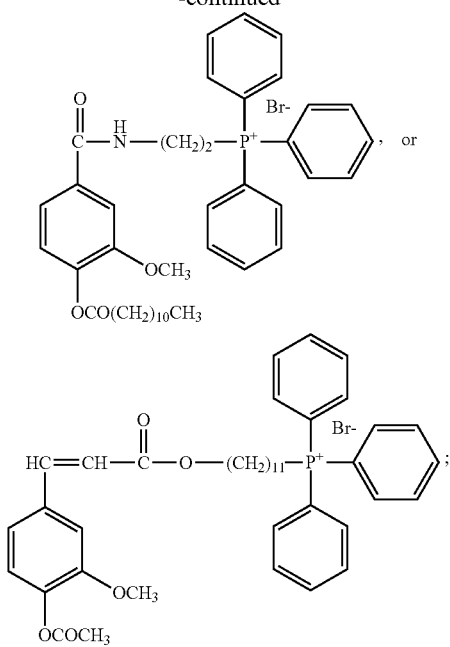

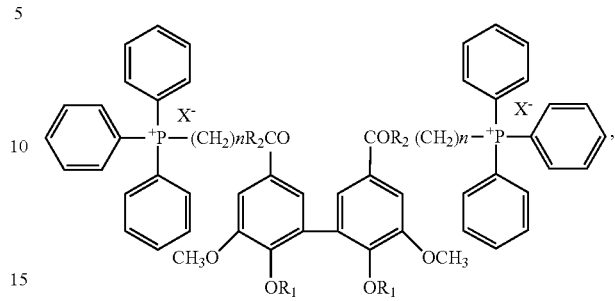

or wherein the apocynin derivative is a prodrug, solvate or hydrate of any of the preceding structures.

7. The apocynin derivative of claim 1 having the structure:

wherein $R_1$ is H, $COCH_3$, or $CO(CH_2)_mCH_3$, wherein $R_2$ is O or NH, wherein $X^-$ is $Br^-$, wherein n is 2-16, and wherein m is 1-16, or a prodrug, salt, solvate or hydrate thereof.

8. The method of claim 4, wherein the apocynin derivative further includes a pharmaceutically suitable carrier system.

9. The method of claim 8, wherein the pharmaceutically suitable carrier system comprises an oral, injection, infusion, inhalation, transdermal, or implant dosage form.

* * * * *

UNITED STATES PATENT AND TRADEMARK OFFICE
CERTIFICATE OF CORRECTION

PATENT NO. : 8,962,600 B2  
APPLICATION NO. : 13/266659  
DATED : February 24, 2015  
INVENTOR(S) : Balaraman Kalyanaraman et al.

It is certified that error appears in the above-identified patent and that said Letters Patent is hereby corrected as shown below:

On the Title page, Item (73) Assignee, the following should be added

-- Iowa State University Research Foundation, Inc., Ames, Iowa --

Signed and Sealed this  
Second Day of February, 2016

Michelle K. Lee  
*Director of the United States Patent and Trademark Office*